(12) United States Patent
Picha et al.

(10) Patent No.: US 11,324,606 B2
(45) Date of Patent: May 10, 2022

(54) SPINAL INTERBODY CAGE COMPRISING A BULK INTERBODY CAGE, A TOP FACE, A BOTTOM FACE, PILLARS, AND SLOTS

(71) Applicant: GARY A. ZWICK, TRUSTEE OF THE EVEREST TRUST UTA APRIL 20, 2017, Cleveland, OH (US)

(72) Inventors: George J. Picha, Brecksville, OH (US); Grant Wesley Phillips, Richfield, OH (US); Rachel Smith, Brecksville, OH (US); James Price, Stow, OH (US); Gregory Causey, Erie, CO (US)

(73) Assignee: Gary A. Zwick, Cleveland, OH (US)

(*) Notice: Subject to any disclaimer, the term of this patent is extended or adjusted under 35 U.S.C. 154(b) by 0 days.

(21) Appl. No.: 16/492,328

(22) PCT Filed: Mar. 8, 2018

(86) PCT No.: PCT/US2018/021506
§ 371 (c)(1),
(2) Date: Sep. 9, 2019

(87) PCT Pub. No.: WO2018/165405
PCT Pub. Date: Sep. 13, 2018

(65) Prior Publication Data
US 2020/0323646 A1 Oct. 15, 2020

Related U.S. Application Data

(60) Provisional application No. 62/469,729, filed on Mar. 10, 2017.

(51) Int. Cl.
*A61F 2/44* (2006.01)
*A61F 2/30* (2006.01)

(52) U.S. Cl.
CPC ............ *A61F 2/4455* (2013.01); *A61F 2/447* (2013.01); *A61F 2/4465* (2013.01); *A61F 2002/30224* (2013.01); *A61F 2002/30263* (2013.01)

(58) Field of Classification Search
CPC ....... A61F 2/4455; A61F 2/4465; A61F 2/447
See application file for complete search history.

(56) References Cited

U.S. PATENT DOCUMENTS 3,605,123 A 9/1971 Hahn
3,808,606 A 5/1974 Tronzo
(Continued)

FOREIGN PATENT DOCUMENTS

CN 106667626 A 5/2017
DE 837294 C 4/1952
(Continued)

OTHER PUBLICATIONS

Bobyn et al., "The Optimum Pore Size for the Fixation of Porous-Surfaced Metal Implants by the Ingrowth of Bone," Clinical Orthopaedics and Related Research, No. 150, pp. 263-270 (1980) (cited in specification on p. 1).
(Continued)

*Primary Examiner* — Julianna N Harvey
(74) *Attorney, Agent, or Firm* — Pearne & Gordon LLP

(57) ABSTRACT

Spinal interbody cages are provided that include a bulk interbody cage, a top face, a bottom face, pillars, and slots. The pillars are for contacting vertebral bodies. The slots are to be occupied by bone of the vertebral bodies and/or by bone of a bone graft. The spinal interbody cage has a Young's modulus of elasticity of at least 3 GPa, and has a ratio of the sum of (i) the volumes of the slots to (ii) the sum of the volumes of the pillars and the volumes of the slots of 0.40:1 to 0.90:1.

20 Claims, 14 Drawing Sheets

(56) References Cited

U.S. PATENT DOCUMENTS

| | | | |
|---|---|---|---|
| 3,855,638 A | 12/1974 | Pilliar | |
| 4,237,559 A | 12/1980 | Borom | |
| 4,608,052 A | 8/1986 | Van Kampen et al. | |
| 4,834,757 A * | 5/1989 | Brantigan | A61B 17/1604 623/17.11 |
| 4,865,603 A | 9/1989 | Noiles | |
| 5,195,892 A | 3/1993 | Gersberg | |
| 5,207,709 A | 5/1993 | Picha | |
| 5,236,453 A | 8/1993 | Picha | |
| 5,263,953 A | 11/1993 | Bagby | |
| 5,312,256 A | 5/1994 | Scortecci | |
| 5,545,226 A | 8/1996 | Wingo et al. | |
| 5,571,185 A | 11/1996 | Schug | |
| 5,628,630 A | 5/1997 | Misch | |
| 5,823,777 A | 10/1998 | Misch | |
| 5,876,457 A | 3/1999 | Picha et al. | |
| 6,001,100 A | 12/1999 | Sherman et al. | |
| 6,071,310 A | 6/2000 | Picha et al. | |
| 6,106,558 A | 8/2000 | Picha | |
| 6,315,562 B1 | 11/2001 | Kumar | |
| 6,346,122 B1 | 2/2002 | Picha et al. | |
| 6,569,201 B2 | 5/2003 | Moumene et al. | |
| 6,789,991 B2 | 9/2004 | Hsu | |
| 6,846,313 B1 | 1/2005 | Rogers et al. | |
| 6,989,032 B2 | 1/2006 | Errico et al. | |
| 7,018,418 B2 | 3/2006 | Amrich et al. | |
| 7,041,140 B2 | 5/2006 | Picha | |
| 7,128,760 B2 | 10/2006 | Michelson | |
| 7,205,051 B2 | 4/2007 | King et al. | |
| 7,250,550 B2 | 7/2007 | Overby et al. | |
| 7,347,873 B2 | 3/2008 | Paul et al. | |
| 7,393,170 B2 | 7/2008 | Chen | |
| 7,556,648 B2 | 7/2009 | Picha et al. | |
| 7,608,107 B2 | 10/2009 | Michelson | |
| 7,691,148 B2 | 4/2010 | Michelson | |
| 7,955,512 B2 | 6/2011 | Park et al. | |
| 8,470,036 B2 | 6/2013 | Barnes et al. | |
| 8,551,173 B2 | 10/2013 | Lechmann et al. | |
| 8,672,940 B2 | 3/2014 | Prager et al. | |
| 8,685,070 B2 | 4/2014 | Rupp et al. | |
| 8,764,831 B2 | 7/2014 | Lechmann et al. | |
| 8,771,354 B2 | 7/2014 | Picha et al. | |
| 8,900,302 B2 | 12/2014 | Gonzalez-Hernandez | |
| 9,198,701 B2 | 12/2015 | Prien et al. | |
| 9,333,081 B2 | 5/2016 | Picha et al. | |
| 9,456,856 B2 | 10/2016 | Ballard | |
| 9,579,206 B2 | 2/2017 | Picha et al. | |
| 9,581,183 B2 | 2/2017 | Lajewardi et al. | |
| 9,801,673 B2 | 10/2017 | Aeschlimann et al. | |
| 9,808,346 B2 | 11/2017 | Stark | |
| 10,154,908 B2 | 12/2018 | Picha et al. | |
| 2001/0039454 A1 | 11/2001 | Ricci et al. | |
| 2002/0040242 A1 | 4/2002 | Picha et al. | |
| 2002/0106393 A1 | 8/2002 | Bianchi et al. | |
| 2004/0093028 A1 | 5/2004 | Ruff | |
| 2004/0122518 A1 | 6/2004 | Rhoda | |
| 2004/0181286 A1 | 9/2004 | Michelson | |
| 2004/0260291 A1 | 12/2004 | Jensen | |
| 2005/0033289 A1 | 2/2005 | Warren et al. | |
| 2005/0049706 A1 | 3/2005 | Brodke et al. | |
| 2005/0246021 A1 | 11/2005 | Ringeisen et al. | |
| 2005/0283158 A1 | 12/2005 | West | |
| 2006/0015184 A1 | 1/2006 | Winterbottom et al. | |
| 2006/0030884 A1 | 2/2006 | Yeung | |
| 2007/0123988 A1 | 5/2007 | Coughlin | |
| 2007/0166124 A1 | 7/2007 | Hsu | |
| 2007/0168037 A1 * | 7/2007 | Posnick | A61F 2/4425 623/17.14 |
| 2008/0109037 A1 | 5/2008 | Steiner | |
| 2008/0287910 A1 | 11/2008 | Picha | |
| 2008/0306554 A1 | 12/2008 | McKinley | |
| 2009/0069904 A1 | 3/2009 | Picha | |
| 2009/0105772 A1 | 4/2009 | Seebeck | |
| 2009/0204214 A1 * | 8/2009 | Fuji | A61F 2/446 623/17.11 |
| 2010/0042167 A1 | 2/2010 | Nebosky et al. | |
| 2010/0211118 A1 | 8/2010 | Christen et al. | |
| 2010/0256758 A1 | 10/2010 | Gordon et al. | |
| 2010/0298950 A1 | 11/2010 | McDonnell et al. | |
| 2011/0093020 A1 | 4/2011 | Wu | |
| 2011/0125264 A1 | 5/2011 | Bagga et al. | |
| 2011/0213467 A1 | 9/2011 | Lozier et al. | |
| 2011/0218585 A1 | 9/2011 | Krinke et al. | |
| 2011/0320000 A1 | 12/2011 | O'Neil et al. | |
| 2012/0271427 A1 | 10/2012 | Serafin | |
| 2013/0090735 A1 * | 4/2013 | Mermuys | A61F 2/447 623/17.16 |
| 2013/0110241 A1 | 5/2013 | Palmatier et al. | |
| 2013/0110255 A1 * | 5/2013 | Picha | A61F 2/30756 623/23.74 |
| 2013/0116793 A1 | 5/2013 | Kloss | |
| 2013/0325129 A1 | 12/2013 | Huang | |
| 2014/0025181 A1 | 1/2014 | Vanasse et al. | |
| 2014/0180432 A1 | 6/2014 | Conway et al. | |
| 2014/0303729 A1 | 10/2014 | Lee | |
| 2015/0305878 A1 | 10/2015 | O'Neil et al. | |
| 2016/0067048 A1 | 3/2016 | Hensley et al. | |
| 2016/0213475 A1 | 7/2016 | Picha et al. | |

FOREIGN PATENT DOCUMENTS

| | | |
|---|---|---|
| DE | 33 22 803 A1 | 1/1985 |
| DE | 103 25 139 A1 | 12/2004 |
| EP | 0 162 604 A1 | 11/1985 |
| EP | 0 269 256 A1 | 6/1988 |
| EP | 2 253 291 A1 | 11/2010 |
| FR | 3 019 032 A1 | 10/2015 |
| GB | 2 181 354 A | 4/1987 |
| WO | 96/40020 A1 | 12/1996 |
| WO | 199640015 A1 | 12/1996 |
| WO | 2002017823 A1 | 3/2002 |
| WO | 2002032345 A2 | 4/2002 |
| WO | 2007/113862 A1 | 10/2007 |
| WO | 2008/070355 A2 | 6/2008 |
| WO | 2009022911 A2 | 2/2009 |
| WO | 2009/034429 A1 | 3/2009 |
| WO | 2009108789 A1 | 9/2009 |
| WO | 2013063069 A1 | 5/2013 |
| WO | 2016018160 A1 | 2/2016 |
| WO | 2016/029254 A1 | 3/2016 |
| WO | 2016082880 A1 | 6/2016 |
| WO | 2016130878 A1 | 8/2016 |
| WO | 2018053403 A1 | 3/2018 |
| WO | 2018165400 A1 | 9/2018 |
| WO | 2018165403 A1 | 9/2018 |
| WO | 2018169929 A1 | 9/2018 |

OTHER PUBLICATIONS

Jain et al., "Advances in Spinal Interbody Cages," Orthop. Surg., vol. 8, p. 278 (abstact only) (Aug. 2016).

Chong et al., "The design evolution of interbody cages in anterior cervical discectomy and fusion: a systematic review," BMC Musculoskeletal Disorders, DOI 10.1186/s12891-015-0546-x, pp. 1-11 (Apr. 25, 2015).

Pawtex, "ConnectSPINE TM) PPM (TM) (Porous Paw Metal) Anterior Cervical Interbody Fusion Case (ACIF)," pp. 1-2, available at http://www.cusmed.com/porous-paw-metal-anterior-cervical-interbody-fusion-cage.html, last accessed Mar. 7, 2018.

Zimmer Biomet, "TM-S Cervial Fusion Device," pp. 1-11, available at http://www.zimmerbiomet.com/medical-professionals/spine/product/tm-s-device.html; last accessed Mar. 7, 2018.

International Search Report and Written Opinion for corresponding International Application No. PCT/US2018/021506 dated May 24, 2018.

Colton et al., "Screws-Form and Function," AOTrauma (Nov. 2012), pp. 1-10.

Hulbert, S.F., et al.; "Materials of Construction for Artificial Bone Segments"; Research in Dental and Medical Materials (Edward Korostoff ed., 1969), pp. 19-67.

(56) References Cited

OTHER PUBLICATIONS

Bobyn, et al.; "Characteristics of bone ingrowth and interface mechanics of a new porous tantalum biomaterial"; The Journal of Bone & Joint Surgery (Br); vol. 81-B, No. 5; Sep. 1999; pp. 907-914.

Itala, A.I., et al.; "Pore Diameter of More Than 100 μm Is Not Requisite for Bone Ingrowth in Rabbits"; 58 Journal of Biomedical Materials Research (Applied Biomaterials); 2001; pp. 679-683.

Briem, D., et al.; "Response of primary fibroblasts and osteoblasts to plasma treated polyetheretherketone (PEEK) surfaces"; 16 Journal of Materials Science Materials in Medicine; 2005; pp. 671-677.

Biomechanics, BME 315; "Elastic anisotropy of bone" (http://silver.neep.wisc.edu/~lakes/BME315N3.pdf—accessed Dec. 8, 2010); p. 1.

Dai, K., "Rational Utilization of the Stress Shielding Effect of Implants"; Biomechanics and Biomaterials in Orthopedics (ed. Dominique G. Poitout, Springer-Verlag London Limited, Singapore, 2004); pp. title, copyright, and 208-215.

McPherson, E.J., "Adult Reconstruction"; Review of Orthopaedics: Expert Consult; Fifth Edition (ed. Mark D. Miller, Saunders Elsevier, U.S., 2008); pp. 312-313, Section 4; "Complications in fixation," subsection a, "Stress shielding".

\* cited by examiner

SPINAL INTERBODY CAGE COMPRISING A BULK INTERBODY CAGE, A TOP FACE, A BOTTOM FACE, PILLARS, AND SLOTS

CROSS-REFERENCE TO RELATED APPLICATIONS

This application claims the benefit of U.S. Provisional Application No. 62/469,729, filed Mar. 10, 2017, the entire disclosure of which is hereby incorporated herein by reference.

FIELD OF THE INVENTION

The invention relates to spinal interbody cages, and more particularly to spinal interbody cages that include a bulk interbody cage, a top face, a bottom face, pillars, and slots.

BACKGROUND OF THE INVENTION

Conventional hard-tissue implants include implants designed to promote in-growth of hard tissue based on forming a tissue/implant interface in which the implant forms a continuous phase and the tissue forms a discontinuous phase, e.g. based on the implant having a concave and/or porous surface into which the hard tissue can grow, and designed to have add-on surface modifications, e.g. modifications added based on sintering.

For example, Van Kampen et al., U.S. Pat. No. 4,608,052, discloses an implant for use in a human body having an integral attachment surface adapted to permit ingrowth of living tissue. The implant surface is defined by a multiplicity of adjacent, generally concave surface parts having intersecting, generally aligned rims defining an inner attachment surface portion and by a multiplicity of spaced posts projecting from the inner attachment surface. Van Kampen also discloses that implants have been provided with porous surfaces, as described in U.S. Pat. Nos. 3,605,123, 3,808, 606, and 3,855,638.

Also for example, J. D. Bobyn et al, 150 Clinical Orthopaedics & Related Research 263 (1980), discloses that a pore size range of approximately 50 to 400 µm provided an optimal or maximal fixation strength (17 MPa) in the shortest time period (8 weeks) with regard to cobalt-base alloy implants with powder-made porous surfaces. Specifically, implants were fabricated based on coating cylindrical rods of cast cobalt-base alloy with cobalt base alloy powder in four particle size ranges. The particle size ranges were as follows: 25 to 45 µm; 45 to 150 µm; 150 to 300 µm; and 300 to 840 µm. The corresponding pore size ranges of the particles were as follows: 20 to 50 µm; 50 to 200 µm; 200 to 400 µm; and 400 to 800 µm, respectively. The particles were then bonded to the rods based on sintering. All implants were manufactured to have a maximal diameter of 4.5 mm and a length of 9.0 mm. The implants were surgically inserted into holes in dog femurs and bone ingrowth was allowed to proceed. After varying periods of time (4, 8, or 12 weeks), the maximum force required to dislodge the implants was determined. Implants with a pore size lower than 50 µm yielded relatively low fixation strengths at all time points, while implants with a pore size higher than 400 µm exhibited relatively high scatter with regard to fixation strengths, thus indicating that a pore size range of approximately 50 to 400 µm provided an optimal or maximal fixation strength.

Conventional hard-tissue implants also include implants having surface texturing, e.g. raised portions and indented portions, barbs, and/or pillars, to promote an interference fit between the implants and adjacent bone, to make it difficult to withdraw the implants from hard tissue, or to more effectively mechanically anchor at an early date or affix into adjoining hard tissue.

For example, Tuke et al., U.K. Pat. Appl. No. GB2181354A, discloses an orthopedic implant having at least one surface area, integral with the adjacent portion of the implant and adapted in use to contact bone. The surface area has a finely patterned conformation composed of a plurality of raised portions separated from each other by indented portions. The indented portions are of a width and depth to allow bone penetration thereinto in use to promote an interference fit between the implant and adjacent bone in the region of the patterned area.

Also for example, Amrich et al., U.S. Pat. No. 7,018,418, discloses implants having a textured surface with microrecesses such that the outer surface overhangs the microrecesses. In one embodiment, unidirectional barbs are produced in the surface that can be inserted into bone or tissue. The directional orientation of the barbs is intended to make it difficult to withdraw from the bone or tissue.

Also for example, Picha, U.S. Pat. No. 7,556,648, discloses a spinal implant, i.e. an implant for use in fusing and stabilizing adjoining spinal vertebrae, including a hollow, generally tubular shell having an exterior lateral surface, a leading end, and a trailing end. The exterior surface includes a plurality of pillars arranged in a non-helical array. Each pillar has a height of 100 to 4,500 µm and a lateral dimension at the widest point of 100 to 4,500 µm. The exterior surface also has a plurality of holes therethrough to permit bone ingrowth therethrough.

Also for example, Paul et al., U.S. Pat. No. 7,347,873, discloses an allogenic intervertebral implant for fusing vertebrae. The implant has a wedge-shaped profile to restore disc height and the natural curvature of the spine. The top and bottom surfaces of the implant have a plurality of teeth to resist expulsion and provide initial stability.

Also for example, Lechmann et al., U.S. Pat. No. 8,764, 831, discloses an intervertebral implant that includes a three-dimensional body in the form of a cage with an upper side and an underside, which are suitable for abutting the end plates of two adjacent vertebral bodies. The upper side and the underside of the three-dimensional body are provided with structuring in the form of teeth.

Also for example, Ballard, U.S. Pat. No. 9,456,856, discloses an intrabody implant for placement between separated portions of a previously-unitary bony structure, such as a vertebral body. The intrabody implant comprises first and second surfaces for engaging the first and second portions of the separated bony structure. The first and second surfaces may comprise a plurality of surface features extending outward from the surfaces to engage a complementary surface of the bony structure. The surface features can include ridges, teeth, pyramidal structures, roughened irregular projections and/or combinations thereof.

Unfortunately, interfaces of hard tissue and hard-tissue implants in which the hard tissue is in a discontinuous phase may be susceptible to stress shielding, resulting in resorption of affected hard tissue, e.g. bone resorption, over time. Also, addition of surface texturing to implants by sintering can result in the surface texturing occupying an excessive volume of corresponding hard tissue/implant interfaces, leaving insufficient space for hard tissue. In addition, implants for hard tissues such as long bone, maxillary bone, mandibular bone, and membranous bone are designed to perform under conditions relevant to those hard tissues, i.e. load bearing conditions, including compression and tension, varying across the hard tissue and across time, and intermittent rotational and vertical shear, rather than conditions relevant to spine, i.e. compression, rotational shear, and vertical shear, with the compression being essentially constant, the rotational shear being intermittent, and the vertical shear being rare.

Picha et al., U.S. Pat. No. 8,771,354, discloses hard-tissue implants including a bulk implant, a face, pillars, and slots. The hard-tissue implant has a Young's modulus of elasticity of at least 10 GPa, has a ratio of (i) the sum of the volumes of the slots to (ii) the sum of the volumes of the pillars and the volumes of the slots of 0.40:1 to 0.90:1, does not comprise any part that is hollow, and does not comprise any non-pillar part extending to or beyond the distal ends of any of the pillars. The hard-tissue implants can provide immediate load transfer upon implantation and prevent stress shielding over time, thus promoting hard-tissue remodeling and growth at the site of implantation. The interface can have a continuous phase corresponding to the hard tissue and a discontinuous phase corresponding to the hard-tissue implant.

Nonetheless, there remains a need for hard-tissue implants that address the issues discussed above and that provide improvements. The spinal interbody cage disclosed herein is such an implant.

BRIEF SUMMARY OF THE INVENTION

A spinal interbody cage is provided that includes a bulk interbody cage, a top face, a bottom face, pillars, and slots. The top face is a top exterior surface of the bulk interbody cage and has a top central opening. The bottom face is a bottom exterior surface of the bulk interbody cage and has a bottom central opening. The pillars are for contacting vertebral bodies. The pillars are distributed on the top face, around the top central opening, and extend distally therefrom. The pillars also are distributed on the bottom face, around the bottom central opening, and extend distally therefrom. The pillars are distributed across areas of at least 25 mm² of each of the top face and the bottom face, respectively. Each pillar is integral to the bulk interbody cage, has a distal end, having a transverse area of (100×100) to (2,000×2,000) µm², and has a height of 100 to 2,500 µm. The slots are to be occupied by bone of the vertebral bodies and/or by bone of a bone graft. The slots are defined by the pillars. The slots intersect between the pillars. Each slot has a width of 100 to 2,500 µm as measured along the shortest distance between adjacent pillars. The spinal interbody cage has a Young's modulus of elasticity of at least 3 GPa, and has a ratio of (i) the sum of the volumes of the slots to (ii) the sum of the volumes of the pillars and the volumes of the slots of 0.40:1 to 0.90:1.

BRIEF DESCRIPTION OF THE DRAWINGS

These and other features, aspects, and advantages of the present disclosure are better understood when the following detailed description is read with reference to the accompanying drawings, in which.

DETAILED DESCRIPTION

Figure 1:
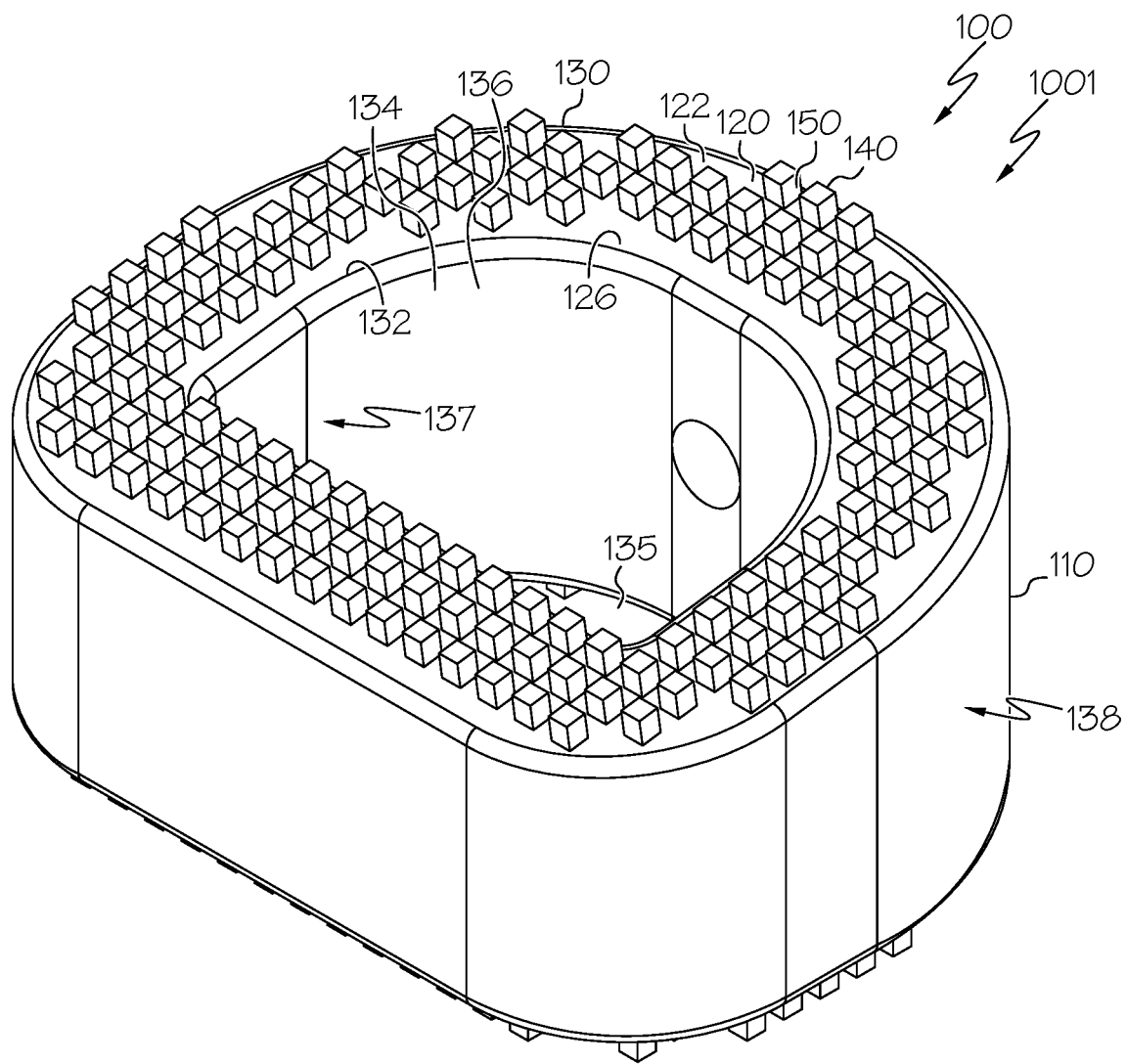
FIG. 1 is a top perspective view of a spinal interbody cage corresponding to an anterior lumbar interbody fusion (ALIF) spinal interbody cage.

As set forth in the figures, example spinal interbody cages are provided. The spinal interbody cages provide advantages, including for example that the spinal interbody cage can promote remodeling and growth of bone of vertebral bodies and/or bone of bone graft at a site of implantation between vertebral bodies, immediate micro-subsidence following implantation in a patient, improved fusion across an entire disc space, and improved resistance to expulsion during healing. Without wishing to be bound by theory, it is believed that these advantages are based on properties of the spinal interbody cages and the interface resulting from implantation thereof.

This is because the interface can have a continuous phase corresponding to the bone of vertebral bodies and/or bone of bone graft and a discontinuous phase corresponding to the spinal interbody cages. The bone of vertebral bodies and/or bone of bone graft can also make up at least 40% of the volume of the interface, and the product of the Young's modulus of elasticity of the bone and the volume of the bone and the product of the Young's modulus of elasticity of the spinal interbody cage and the volume of the pillars of the spinal interbody cage can be well matched. Thus, the interface can exhibit mechanical properties similar to those of the bulk bone of the vertebral bodies adjacent to the interface. Also, the pillars of the spinal interbody cages potentially may be pressed into bone of vertebral bodies, potentially eliminating micro-motion and migration of the implant over time, accommodating torque, and/or eliminating the need for adhesives such as cement or grout to hold the spinal interbody cages in place. In addition, the spinal interbody cages may promote rich vascularization of the bone of the interface, enhancing wound healing, providing nutritional support, accelerating healing, remodeling, and integration of the bone, and limiting the potential for infection of the bone. Rapid or immediate integration of the bone into the space between the pillars of the spinal interbody cage may also prevent detrimental cellular reactions at the interface, such as formation of fibrous tissue, seroma, or thrombosis.

It is believed that implantation of the spinal interbody cage between adjacent vertebral bodies will result in the pillars of the spinal interbody cage contacting the vertebral bodies, e.g. bone of the vertebral bodies, and more particularly bone of endplates of the vertebral bodies. In some cases the pillars may initially penetrate the bone of the vertebral bodies upon implantation of the spinal interbody cage. Alternatively or additionally, in some cases the pillars may penetrate the bone of the vertebral bodies later, under physiological loading, e.g. such as when a patient in which the spinal interbody cage has been implanted stands and the spinal interbody cage thus experiences the body weight of the patient. Also alternatively or additionally, over time bone of vertebral bodies and/or bone of bone graft may grow in and around the pillars, thus occupying slots between the pillars, e.g. during healing.

It is believed that the interface resulting from implantation of the spinal interbody cage into bone of vertebral bodies will be, or can become, an interface that is continuous with respect to the bone and discontinuous with respect to the spinal interbody cage, across an area of the top face and the bottom face of the spinal interbody cage from which the pillars extend. Such an interface will exhibit properties similar to those of the bulk bone of vertebral bodies adjacent to the interface, e.g. high resilience to compression, which occurs essentially constantly, rotational shear, which occurs intermittently, and vertical shear, which occurs rarely but which is important too, providing advantages in spinal applications.

As used herein, the term "spinal interbody cage" means an implant having a cage structure, e.g. a structure having a generally cuboidal shape, among other possible shapes, and an open architecture, e.g. at least two openings and a central cavity extending therebetween, suitable for implantation between adjacent vertebral bodies. Exemplary spinal interbody fusion cages can be used in a variety of spinal interbody fusion applications. Exemplary spinal interbody cages include an anterior lumbar interbody fusion (ALIF) spinal interbody cage, a posterior lumbar interbody fusion (PLIF) spinal interbody cage, a lateral spinal interbody cage, a direct lateral interbody fusion (DLIF) spinal interbody cage, a transforaminal lumbar interbody fusion (TLIF) spinal interbody cage, an extreme lateral interbody fusion (XLIF) spinal interbody cage, and a cervical spinal interbody cage, among others.

The spinal interbody cages can be placed, for example, in cervical spine, thoracic spine, or lumbar spine. Exemplary adjacent vertebral bodies suitable for implantation of the spinal interbody cage include adjacent vertebral bodies from among C2-T1 vertebrae, adjacent vertebral bodies from among T1-T12 vertebrae, adjacent vertebral bodies of L4-L5 vertebra, and adjacent vertebral bodies of L5-S1 vertebrae, among others.

As used herein, the term "pillar" means a projection that extends distally from a surface of a spinal interbody cage, e.g. from a top face and/or a bottom face of the spinal interbody cage, that is not in direct physical contact with any other pillars or other parts of the spinal interbody cage other than the surface, and that is for contacting a vertebral body. Because a pillar is not in direct physical contact with any other pillars or other parts of the spinal interbody cage other than the surface, upon implantation no pillar forms a continuous phase within the resulting interface of the vertebral body and spinal interbody cage. A pillar can have a transverse area, i.e. an area of a cross-section taken relative to a vertical axis along which the pillar extends distally from the face of the implant, of, for example, (i) (100 µm×100 µm) to (2,000 µm×2,000 µm), i.e. $1.0 \times 10^4$ µm$^2$ to $4.0 \times 10^6$ µm$^2$, (ii) (250 µm×250 µm) to (1,000 µm×1,000 µm), i.e. $6.3 \times 10^4$ µm$^2$ to $1.0 \times 10^6$ µm$^2$, (iii) (300 µm×300 µm) to (500 µm×500 µm), i.e. $9 \times 10^4$ µm$^2$ to $2.5 \times 10^5$ µm$^2$, (iv) (350 µm×350 µm) to (450 µm×450 µm), i.e. $1.2 \times 10^5$ µm$^2$ to $2.0 \times 10^5$ µm$^2$, or (v) (395 µm×395 µm) to (405 µm×405 µm), i.e. $1.6 \times 10^5$ µm$^2$. Of note, the expression of transverse areas of pillars as squares of linear dimensions, e.g. (100 µm×100 µm), here and throughout this application, is for purposes of convenience only and is not intended to limit any pillars so described to square shapes, square transverse areas, or square cross-sections. A pillar can have a pillar height, i.e. the height of the pillar from the face of the spinal interbody cage to the distal end of the pillar, of, for example, 100 to 2,500 µm, 200 to 1,000 µm, 400 to 600 µm, 450 to 550 µm, 490 to 510 µm, or 500 µm. A pillar can have a volume corresponding to the product of pillar transverse area and pillar height. A pillar can have, as seen from a top view, a square shape, a rectangular shape, a herringbone shape, a circular shape, or an oval shape, respectively, or alternatively can have other polygonal, curvilinear, or variable shapes.

As used herein, the term "slot" means the spaces between the pillars. Accordingly, the pillars define the slots. The slots can have a slot height as defined by the pillars, of, for example, 100 to 2,500 µm, 200 to 1,000 µm, 400 to 600 µm, 450 to 550 µm, 490 to 510 µm, or 500 µm. The slots can have a slot width as measured along the shortest distance between adjacent pillars of, for example, 100 to 2,500 µm, 150 to 1,000 µm, 175 to 450 µm, 190 to 410 µm, 190 to 210 µm, or 390 to 410 µm. The slots have a volume corresponding to the volume of the space between the pillars.

As used herein, the term "pore" refers to a void space of less than 1,000 µm in size, i.e. having a diameter of less than 1,000 µm, on or below a surface, e.g. the surface of a spinal interbody cage. Pores can occur in a material naturally, e.g. based on a natural porosity of the material, or can be introduced, e.g. by chemical or physical treatment. Pores can be continuous with respect to each other, based on being interconnected with each other below a surface, or pores can be discontinuous, based on not being interconnected with each other below a surface. Pores can be sufficiently large to allow for migration and proliferation of osteoblasts and mesenchymal cells. Accordingly, for example, a porous surface is a surface that includes void spaces of less than 1,000 μm in size in the surface, whereas a non-porous surface is a surface that does not include such a void space.

As used herein, the term "interface resulting from implantation of the spinal interbody cage into bone of vertebral bodies," or more simply "interface," means the product of implantation wherein the pillars of the spinal interbody cage are contacting vertebral bodies and the slots of the spinal interbody cage are occupied, partially or completely, by bone of vertebral bodies and/or bone of bone graft. The interface includes the pillars, bone that occupies the slots of the spinal interbody cage, any remaining unoccupied space in the slots, any bone that occupies any additional space between the face of the spinal interbody cage and a plane defined by the distal ends of the pillars, and any bone that occupies any pores on the face or the pillars. Accordingly, the interface boundaries are the face of the spinal interbody cage, the internal surfaces of any pores on the face, and the bulk bone surrounding the interface.

In some example embodiments, e.g. immediately after implanting the spinal interbody cage between adjacent vertebral bodies with at least some penetration of the pillars into bone of the vertebral bodies and/or after at least some remodeling and growth of the bone of vertebral bodies and/or bone graft to partially fill in space between the spinal interbody cage and the bone, the pillars are contacting the vertebral bodies (e.g. at distal ends of the pillars), and the slots are partially occupied by the bone. In other example embodiments, e.g. after implanting the spinal interbody cage between adjacent vertebral bodies and further after extensive remodeling and growth of the bone of vertebral bodies and/or bone of bone graft to fill in all space between the spinal interbody cage and the bone, the pillars are contacting the vertebral bodies (e.g. at distal ends and lateral surfaces of the pillars), and the slots are completely occupied by the bone of vertebral bodies and/or bone of bone graft. In other example embodiments, the pillars contact bone of vertebral bodies and/or bone of bone graft over time, based on remodeling and growth of bone of vertebral bodies and/or bone of bone graft in and around the pillars, e.g. during healing.

As used herein, the term "continuous," when used for example in reference to the bone of vertebral bodies and/or bone of bone graft of an interface, means that the bone forms a single continuous phase, extending throughout and across the interface to each boundary of the interface. As used herein, the term "discontinuous," when used for example in reference to the spinal interbody cage of an interface, means that the spinal interbody cage does not form such a single continuous phase.

Figure 2:
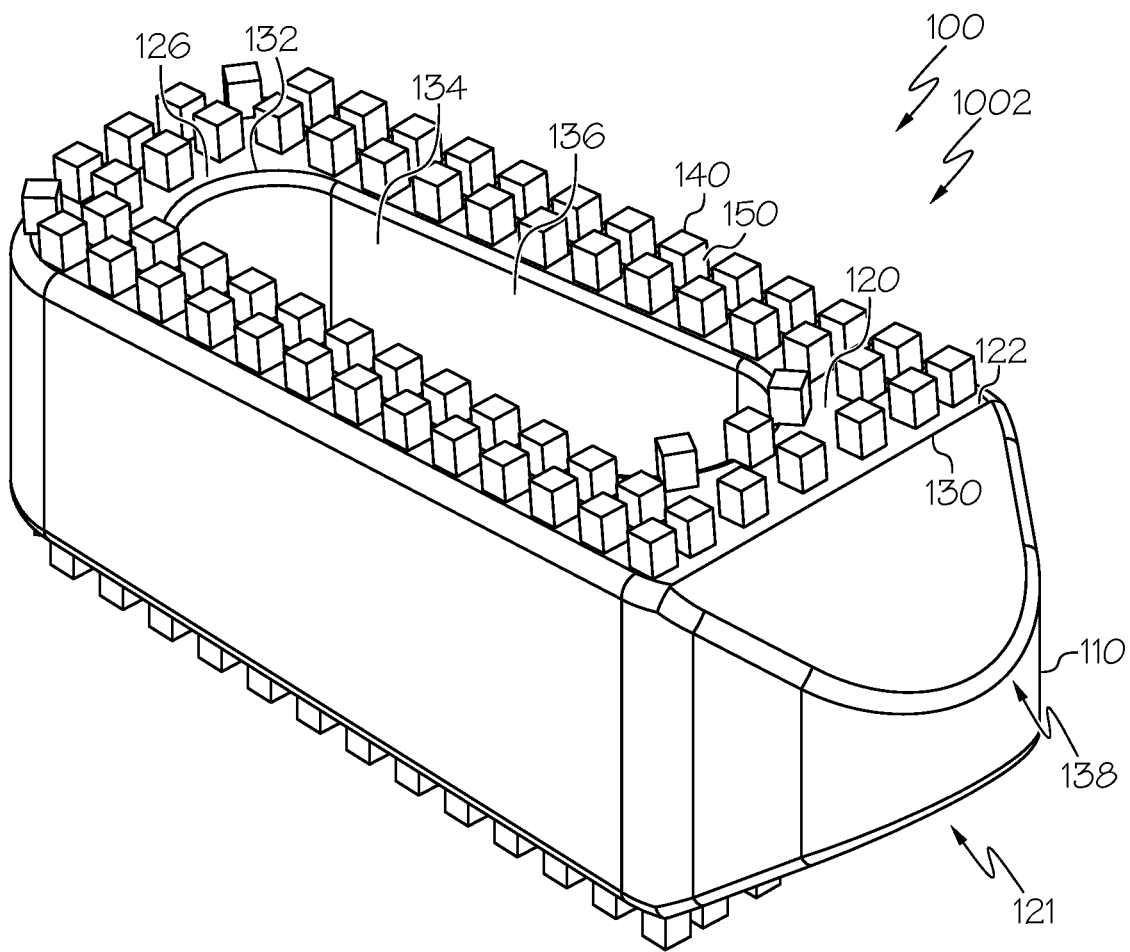
FIG. 2 is a top perspective view of a spinal interbody cage corresponding to a posterior lumbar interbody fusion (PLIF) spinal interbody cage.

Considering the features of an example spinal interbody cages in more detail, FIG. 1 and FIG. 2 provide illustrations in perspective view of various example spinal interbody cages 100, corresponding to an anterior lumbar interbody fusion (ALIF) spinal interbody cage 1001 and a posterior lumbar interbody fusion (PLIF) spinal interbody cage 1002. Additional views of the ALIF spinal interbody cage 1001 are shown in FIGS. 10-14. Additional views of the PLIF spinal interbody cage 1002 are shown in FIGS. 15-19.

The spinal interbody cage 100 can be made from a material having a Young's modulus of elasticity, i.e. a tensile modulus of elasticity, of at least 3 GPa, as measured at 21° C. The spinal interbody cage 100 can be made, for example, from one or more materials such as implantable-grade polyaryletherketone that is essentially unfilled (such as implantable-grade polyetheretherketone or implantable-grade polyetherketoneketone), titanium, stainless steel, cobalt-chromium alloy, titanium alloy (such as Ti-6Al-4V titanium alloy or Ti-6Al-7Nb titanium alloy), ceramic material (such as silicon nitride (Si3N4)), or implantable-grade composite material (such as implantable-grade polyaryletherketone with filler, implantable-grade polyetheretherketone with filler, implantable-grade polyetheretherketone with carbon fiber, or implantable-grade polyetheretherketone with hydroxyapatite). Specific examples include (i) implantable-grade polyetheretherketone that is essentially unfilled, which has a Young's modulus of approximately 4 GPa, (ii) implantable-grade polyetheretherketone with filler, e.g. carbon-fiber-reinforced implantable-grade polyetheretherketone, which has a Young's modulus of elasticity of at least 18 GPa, (iii) titanium, which has a Young's modulus of elasticity of approximately 110 GPa, (iv) stainless steel, which has a Young's modulus of elasticity of approximately 200 GPa, (v) cobalt-chromium alloy, which has a Young's modulus of elasticity of greater than 200 GPa, or (vi) titanium alloy, which has a Young's modulus of elasticity of approximately 105-120 GPa, all as measured at 21° C. The spinal interbody cage 100 also can be made, for example, from one or more hard tissues such as a hard tissue obtained from a human or animal (such as autologous hard tissue, allogenic hard tissue, or xenogeneic hard tissue), human cartilage, animal cartilage, human bone, animal bone, cadaver bone, or cortical allograft. Such hard tissues obtained from a human or animal can have a Young's modulus of elasticity of, e.g. 4 to 18 GPa. Such hard tissues obtained from a human or animal can also be treated, in advance of implantation, to decrease or eliminate the capacity of the hard tissue to elicit an immune response in an individual upon implantation into the individual. The spinal interbody cage 100 also can be made, for example, from one or more materials such as resin for rapid prototyping, SOMOS® NanoTool non-crystalline composite material, SOMOS® 9120 liquid photopolymer, SOMOS® WaterShed XC 11122 resin, ACCURA® XTREM™ White 200 plastic, or ACCURA® 60 plastic. The spinal interbody cage 100 also can be made from further combinations of the above-noted materials and/or hard tissues. Accordingly, the spinal interbody cage 100 has a Young's modulus of elasticity of at least 3 GPa, for example 18 to 230 GPa, 18 to 25 GPa, 100 to 110 GPa, 190 to 210 GPa, 200 to 230 GPa, 105 to 120 GPa, or 4 to 18 GPa.

As shown in FIG. 1, FIG. 2, FIG. 10, FIG. 11, FIG. 15, and FIG. 16, the spinal interbody cage 100 includes a bulk interbody cage 110, a top face 120, a bottom face 121, pillars 140, and slots 150.

Figure 3:
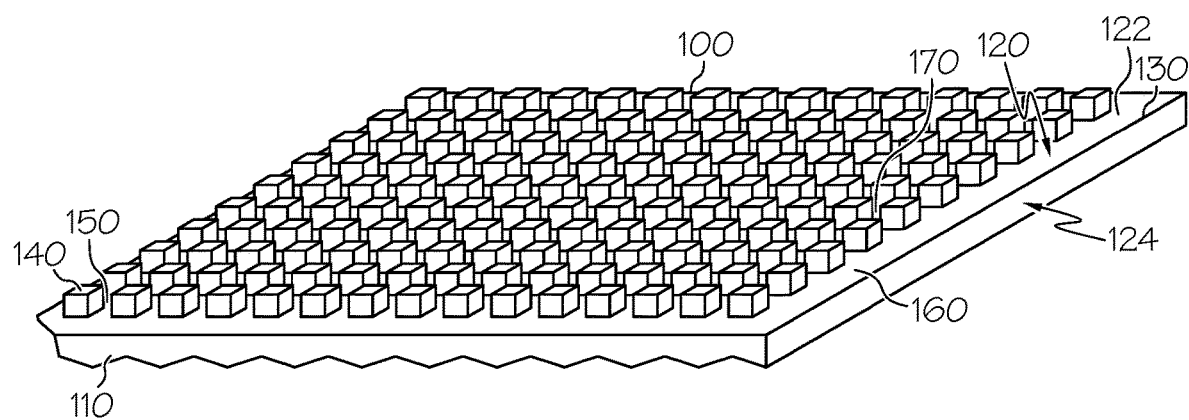
FIG. 3 is a schematic perspective view of a portion of a spinal interbody cage including pillars.

Considering the bulk interbody cage 110 in more detail, as shown in FIG. 3, the bulk interbody cage 110 forms the core of the spinal interbody cage 100 and can have a generally cuboidal shape, although other three-dimensional shapes may be used in further examples. The bulk interbody cage 110 can include at least two openings, e.g. a top central opening 134 and a bottom central opening 135, as discussed below, and a central cavity 136 extending therebetween. The bulk interbody cage 110 can be made from one or more of the materials or hard tissues noted above with respect to the spinal interbody cage 100, e.g. one or more materials such as implantable-grade polyaryletherketone that is essentially unfilled (such as implantable-grade polyetheretherketone or implantable-grade polyetherketoneketone), titanium, stainless steel, cobalt-chromium alloy, titanium alloy (such as Ti-6Al-4V titanium alloy or Ti-6Al-7Nb titanium alloy), ceramic material (such as silicon nitride (Si3N4)), or implantable-grade composite material (such as implantable-grade polyaryletherketone with filler, implantable-grade polyetheretherketone with filler, implantable-grade polyetheretherketone with carbon fiber, or implantable-grade polyetheretherketone with hydroxyapatite), or e.g. one or more hard tissues such as a hard tissue obtained from a human or animal (such as autologous hard tissue, allogenic hard tissue, or xenogeneic hard tissue), human cartilage, animal cartilage, human bone, animal bone, cadaver bone, or cortical allograft, or e.g. one or more materials such as resin for rapid prototyping, SOMOS® NanoTool non-crystalline composite material, SOMOS® 9120 liquid photopolymer, SOMO® WaterShed XC 11122 resin, ACCURA® XTREME™ White 200 plastic, or ACCURA® 60 plastic.

The bulk interbody cage 110 can be porous or non-porous. For example, the bulk interbody cage 110 can include one or more surfaces that are porous, and/or can be made from one or more materials that are porous. Such porous surfaces can include pores having diameters of, e.g. 1 to 900 µm, 100 to 800 µm or 200 to 600 µm. Also for example, the bulk interbody cage 110 can include only surfaces that are non-porous, and/or can be made only from one or more materials that are non-porous.

Considering now the top face 120 in more detail, as shown in FIG. 1 and FIG. 3, the top face 120 of the spinal interbody cage 100 is an exterior surface of the bulk interbody cage 110, having a top central opening 134. The top face 120 has a total area 160, not including an area of the top central opening 134 As shown in FIG. 3, the top face 120 can be flat, i.e. have a flat contour, or can have curvilinear, angular, and/or irregular contours. As shown in FIG. 3, the top face 120 can be defined by an outer edge 130 and an inner edge 132. As shown in FIG. 3, the outer edge 130 and the pillars 140 closest to the outer edge 130 can define an outer peripheral border 122 of the top face 120. Likewise, the inner edge 132 and the pillars 140 closest to the inner edge 132 can define an inner peripheral border 126 of the top face 120. As shown in FIG. 3, the outer edge 130 can define an intersection between the top face 120 and one or more adjacent faces 124 of the spinal interbody cage 100. The top face 120 and the one or more adjacent faces 124 may intersect at the edge 130 at a right angle, although the top face 120 and the one or more adjacent faces 124 may also intersect at other angles, e.g. acute angles, obtuse angles, or varying angles. The outer edge 130 can be sharp, although other rounded, angular, smooth, and/or irregular edges may be used in further examples. The top face 120 can be porous, e.g. including pores having diameters of, e.g. 1 to 900 µm, 100 to 800 µm, or 200 to 600 µm, or the top face 120 can be non-porous.

The bottom face 121 is a bottom exterior surface, having a bottom central opening 135. The bottom face 121 has a total area 161, not including an area of the bottom central opening 135. The bottom face 121 can have a similar layout as the top face 120, as described above and as follows, including an outer edge 131, and inner edge 133, an outer peripheral border 123, and an inner peripheral border 127, like the corresponding ones of the top face 120, among other similarities.

Considering now the pillars 140 in more detail, the pillars 140 are for contacting vertebral bodies. The vertebral bodies can also be selected, for example, from the group consisting of adjacent vertebral bodies from among C2-T1 vertebrae, adjacent vertebral bodies from among T1-T12 vertebrae, adjacent vertebral bodies of L4-L5 vertebra, and adjacent vertebral bodies of L5-S1 vertebrae. In some examples, the pillars 140 may contact a vertebral body immediately upon implantation, e.g. based on extending distally from a top face 120 or a bottom face 121 of the spinal interbody cage 100. In some examples, the pillars 140 may contact a vertebral body over time after implantation, e.g. based on remodeling and growth of bone of vertebral bodies and/or bone of bone graft to come in contact with pillars 140 for which distal ends 430 of the pillars 140 are recessed relative to a surrounding surface of the spinal interbody cage 100.

Figure 4:
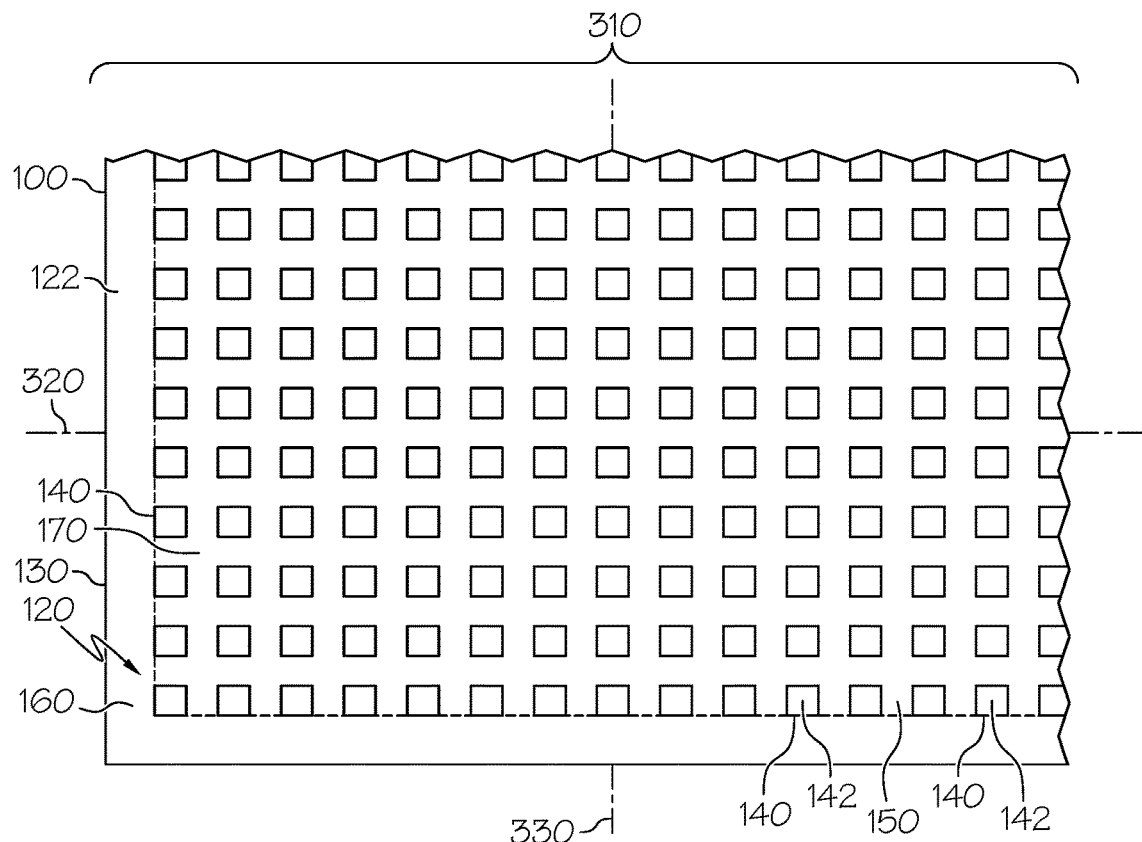
FIG. 4 is a schematic top plan view of a portion of a spinal interbody cage including pillars.

As shown in FIG. 4, the pillars 140 are distributed on the top face 120 of the spinal interbody cage 100, around the top central opening 134, across an area 170 of the top face 120 of at least 25 mm$^2$. For example, the pillars 140 can be distributed in a regular pattern 310 on the top face 120 of the spinal interbody cage 100, across the area 170 of the top face 120. In this regard, the pillars 140 can be distributed in even rows along a horizontal axis 320 and a vertical axis 330 of the top face 120, and can be distributed along a given row uniformly with respect to the distances between the centers 142 of the pillars 140 in the row. Also for example, the pillars 140 can also be distributed in other regular patterns, e.g. the pillars 140 can be distributed in rows that are even with respect to the horizontal axis 320 but not the vertical axis 330, or vice versa, the pillars 140 in one row may be offset from the pillars 140 in adjacent rows, the pillars 140 may be arranged in a spiral pattern, etc. Also for example, the pillars 140 can be distributed on the top face 120 of the spinal interbody cage 100 in irregular patterns or randomly. For example, the pillars 140 can be distributed on the top face 120 of the spinal interbody cage 100 such that the pillars 140 are packed more densely on one area of the top face 120 and less densely on another area of the top face 120.

The pillars 140 also are distributed on the bottom face 121, around the bottom central opening 135, across an area of at least 25 mm$^2$, of the bottom face 121. The pillars 140 can be distributed on the bottom face 121 similarly as on the top face 120, as described above and as follows.

The pillars 140 can be distributed on the top face 120 of the spinal interbody cage 100 such that none of the pillars 140 are located at an outer edge 130 and/or an inner edge 131, i.e. the face 120 can have an outer peripheral border 122 and an inner peripheral border 123 that are not occupied by any pillars 140, resulting in the area 170 of the top face 120 across which the pillars 140 are distributed being less than the total area 160 of the top face 120. In other example embodiments the pillars 140 can be distributed on the top face 120 of the spinal interbody cage 100 such that at least some of the pillars 140 are located at an outer edge 130 or an inner edge 131, e.g. the area 170 of the top face 120 across which the pillars 140 are distributed can be equal to the total area 160 of the top face 120. The same applies regarding the pillars 140 distributed on the bottom face 121.

Figure 5:
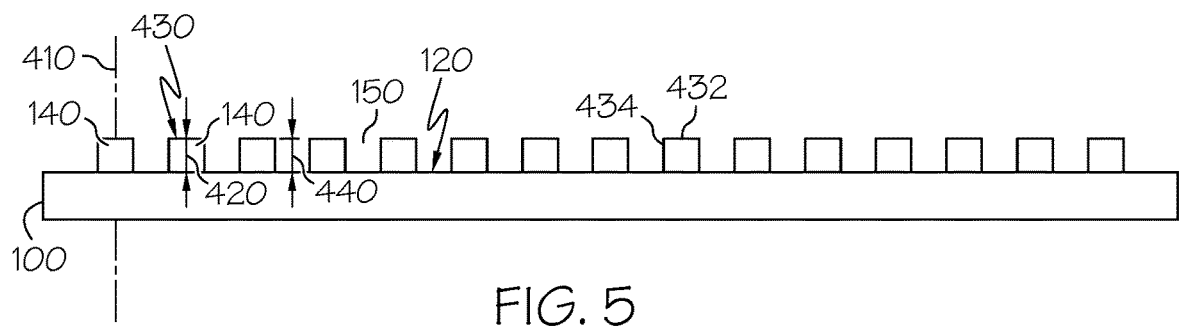
FIG. 5 is a schematic side elevational view of a portion of a spinal interbody cage including pillars.

As shown in FIG. 5, the pillars 140 extend distally from the top face 120 of the spinal interbody cage 100. For example, the pillars 140 can extend distally along a vertical axis 410 from the top face 120 of the spinal interbody cage 100. As shown, the pillars 140 can extend in a uniform direction, i.e. all pillars 140 extend distally at the same angle with respect to the top face 120 and in the same direction. Also for example, some pillars 140 may extend distally at a different angle and/or in a different direction relative to other pillars 140, for example for a spinal interbody cage 100 for which the top face 120 is not flat. As also shown, the pillars 140 can be perpendicular to the top face 120, e.g. extending perpendicularly from the top face 120. Also for example, the pillars 140 can extend from the top face 120 at other angles and/or varying angles. The same applies regarding the pillars 140 extending distally from the bottom face 121.

As shown in FIG. 3, each pillar 140 is integral to the bulk interbody cage 110, i.e. the pillars 140 and the bulk interbody cage 110 are made from the same starting material, rather than, for example, the pillars 140 being an add-on to the bulk interbody cage 110. Like the bulk interbody cage 110, the pillars 140 can be porous, e.g. including pores having diameters of, e.g. 1 to 900 µm, 100 to 800 µm, or 200 to 600 µm, or the pillars 140 can be non-porous.

As shown in FIG. 5, each pillar 140 has a distal end 430, corresponding to the distal-most portion of the pillar 140 relative to the top face 120 of the spinal interbody cage 100. Each pillar 140 can have distal edges 432, corresponding to edges defining the distal end 430 of each pillar 140. Each pillar 140 can also have lateral edges 434, corresponding to edges of the lateral sides of each pillar 140. The distal edges 432 and/or the lateral edges 434 can be sharp, although other rounded, angular, smooth, and/or irregular edges may be used in further examples.

Figure 6A:
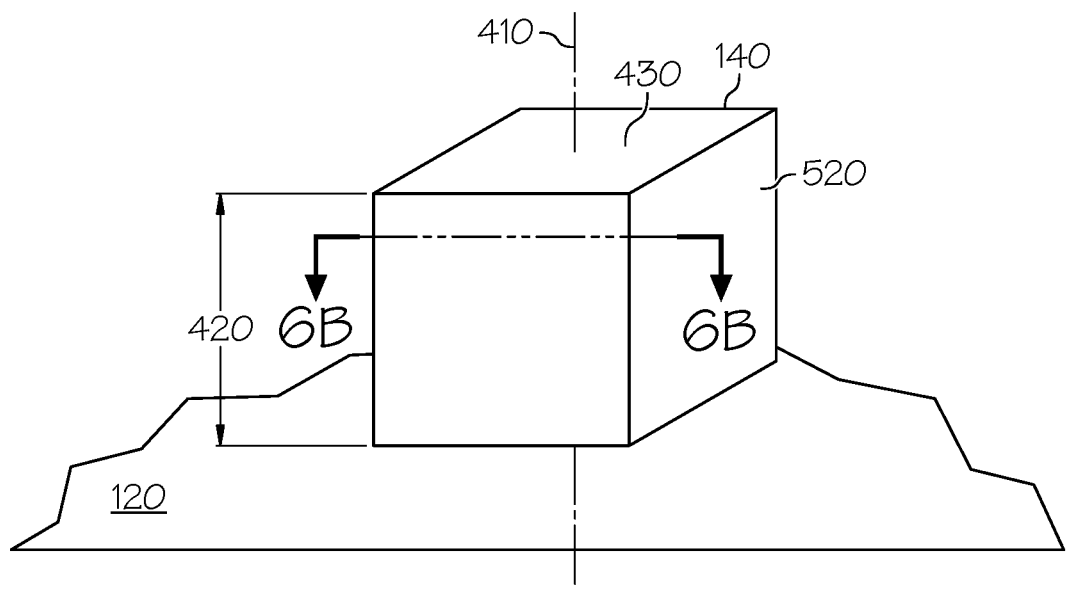
FIG. 6A is a schematic perspective view of a pillar of a spinal interbody cage.
Figure 6B:
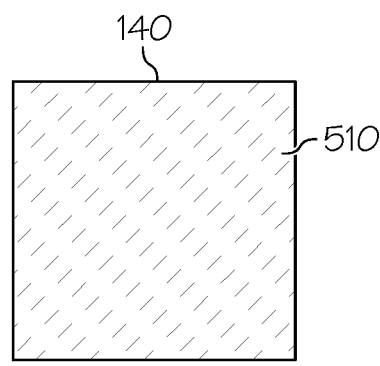
FIG. 6B is a schematic cross-sectional view of a pillar of a spinal interbody cage.
Figure 7A:
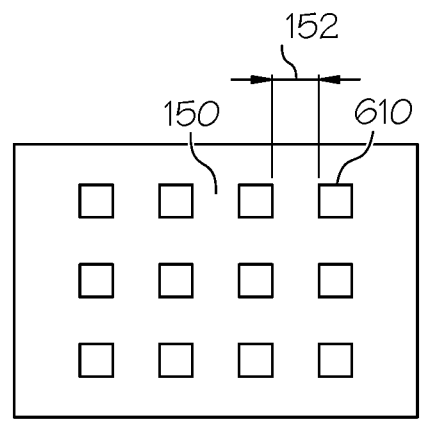
FIGS. 7A-E are schematic top plan views of portions of spinal interbody cage including pillars in which the circumference of the transverse area of the pillars thereof have (A) a square shape, (B) a rectangular shape, (C) a herringbone shape, (D) a circular shape, and (E) an oval shape.
Figure 7B:
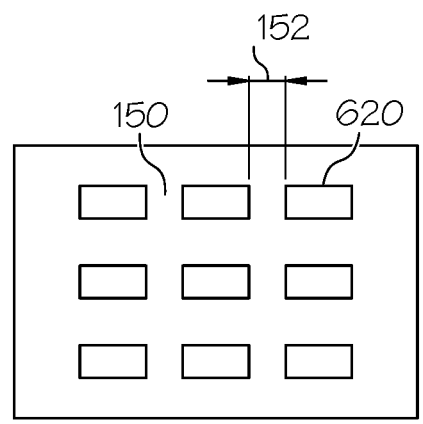
Figure 7C:
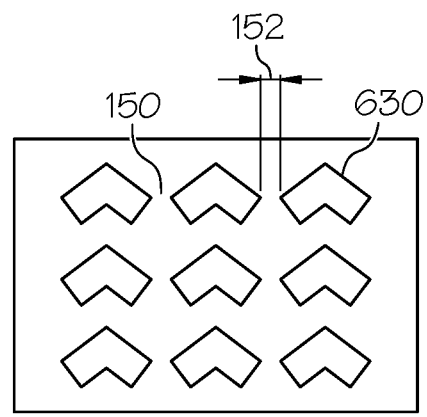
Figure 7D:
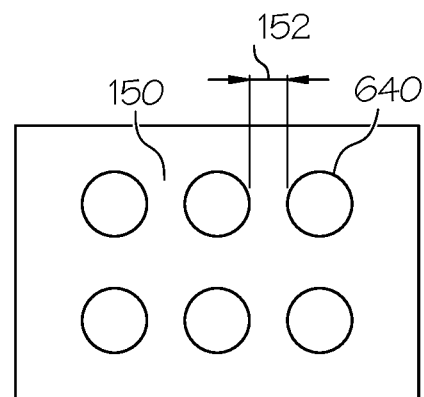
Figure 7E:
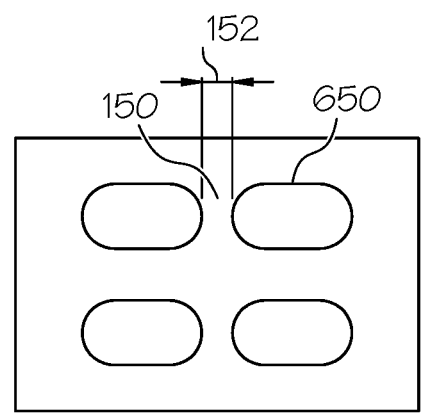

With respect to dimensions of the pillars 140, as shown in FIG. 6A and FIG. 6B, each pillar 140 has a transverse area 510, i.e. an area of a cross-section taken relative to the vertical axis 410 along which the pillar 140 extends distally from the top face 120 or the bottom face 121 of, for example, (100 µm×100 µm) to (2,000 µm×2,000 µm), i.e. $1.0\times10^4$ µm$^2$ to $4.0\times10^6$ µm$^2$, (ii) (250 µm×250 µm) to (1,000 µm×1,000 µm), i.e. $6.3\times10^4$ µm$^2$ to $1.0\times10^6$ µm$^2$, (iii) (300 µm×300 µm) to (500 µm×500 µm), i.e. $9\times10^4$ µm$^2$ to $2.5\times10^5$ µm$^2$, (iv) (350 µm×350 µm) to (450 µm×450 µm), i.e. $1.2\times10^5$ µm$^2$ to $2.0\times10^5$ µm$^2$, or (v) (395 µm×395 µm) to (405 µm×405 µm), i.e. $1.6\times10^5$ µm$^2$. As shown in FIG. 5 and FIG. 6B, each pillar 140 has a pillar height 420, i.e. the height of the pillar 140 from the face 120 of the spinal interbody cage 100 to the distal end 430 of the pillar 140, of, for example, 100 to 2,500 µm, 200 to 1,000 µm, 400 to 600 µm, 450 to 550 µm, 490 to 510 µm, or 500 µm. As shown in FIG. 6A, each pillar 140 has a volume 520, i.e. product of pillar transverse area 510 and pillar height 420.

As shown in FIG. 1 and FIG. 3, the pillars 140 extending from the top face 120 or the bottom face 121 can, for example, all have identical dimensions, e.g. identical pillar transverse areas 510, pillars heights 420, and thus identical individual volumes.

Alternatively, one or more pillars 140 can have dimensions that differ from those of other pillars 140, such that the pillar transverse areas 510 and/or pillar heights 420, and thus volumes, of the one or more pillars 140 differ from those of the other pillars 140. In such cases, the spinal interbody cage 100 can provide an endplate profile based on the pillar heights 420 of the one or more pillars 140 differing from those of the other pillars 140, and the spinal interbody cage 100 can have a parallel height.

Turning to FIG. 7A to FIG. 7E, the pillars 140 can have, as seen from a top view, a square shape, a rectangular shape, a herringbone shape, a circular shape, or an oval shape, or alternatively can have other polygonal, curvilinear, or variable shapes. For example, in some embodiments all pillars 140 can have the same shape, e.g. a square shape, a rectangular shape, a herringbone shape, a circular shape, or an oval shape, as seen from a top view. Also for example, in some embodiments not all pillars 140 have the same shape as seen from a top view.

Considering now the slots 150 in more detail, the slots 150 are to be occupied by the bone of vertebral bodies and/or bone of bone graft. For example, upon implantation of the spinal interbody cage 100 between adjacent vertebral bodies, the bone can immediately occupy at least part of the space corresponding to the slots 150. This can be accomplished, for example, based on penetration of the pillars 140 of the spinal interbody cage 100 into the bone of vertebral bodies to at least some extent. Moreover, bone of vertebral bodies and/or bone of bone graft can eventually occupy part or all of the space corresponding to the slots 150 based on remodeling and/or growth of the bone over time, e.g. based on growth of bone during healing.

As shown in FIG. 3, FIG. 4, and FIG. 5, the pillars 140 define the slots 150 therebetween, i.e. the slots 150 are the spaces between the pillars 140. Accordingly, as shown in FIG. 5, the slots 150 have a slot height 440 as defined by the pillars 140, of, for example, 100 to 2,500 µm, 200 to 1,000 µm, 400 to 600 µm, 450 to 550 µm, 490 to 510 µm, or 500 µm. As shown in FIG. 7A to FIG. 7E, the slots 150 have a slot width 152 as measured along the shortest distance between adjacent pillars 140 of, for example, 100 to 2,500 µm, 150 to 1,000 µm, 175 to 450 µm, 190 to 410 µm, 190 to 210 µm, or 390 to 410 µm. The slots 150 have a volume 710 corresponding to the volume of the space between the pillars 140.

The slots 150 intersect between the pillars 140. Accordingly, the spinal interbody cage 100 includes a plurality of adjacent rows or other groupings of the pillars 140.

The spinal interbody cage 100 has a ratio of (i) the sum of the volumes 710 of the slots 150 to (ii) the sum of the volumes 520 of the pillars 140 and the volumes 710 of the slots 150, of, for example, 0.40:1 to 0.90:1, 0.51:1 to 0.90:1, 0.51:1 to 0.60:1, or 0.70:1 to 0.76:1. Without wishing to be bound by theory, it is believed that this ratio determines the approximate percentages of bone of vertebral bodies and/or bone of bone graft and spinal interbody cage 100 that will occupy the interface following implantation of the spinal interbody cage 100, e.g. that upon penetration of pillars 140 of the spinal interbody cage 100 into the bone of vertebral bodies and/or upon remodeling and growth of the bone of vertebral bodies and/or bone of bone graft following implantation, that the bone will occupy all or essentially all of the space corresponding to the slots 150 of the spinal interbody cage 100.

Figure 8:
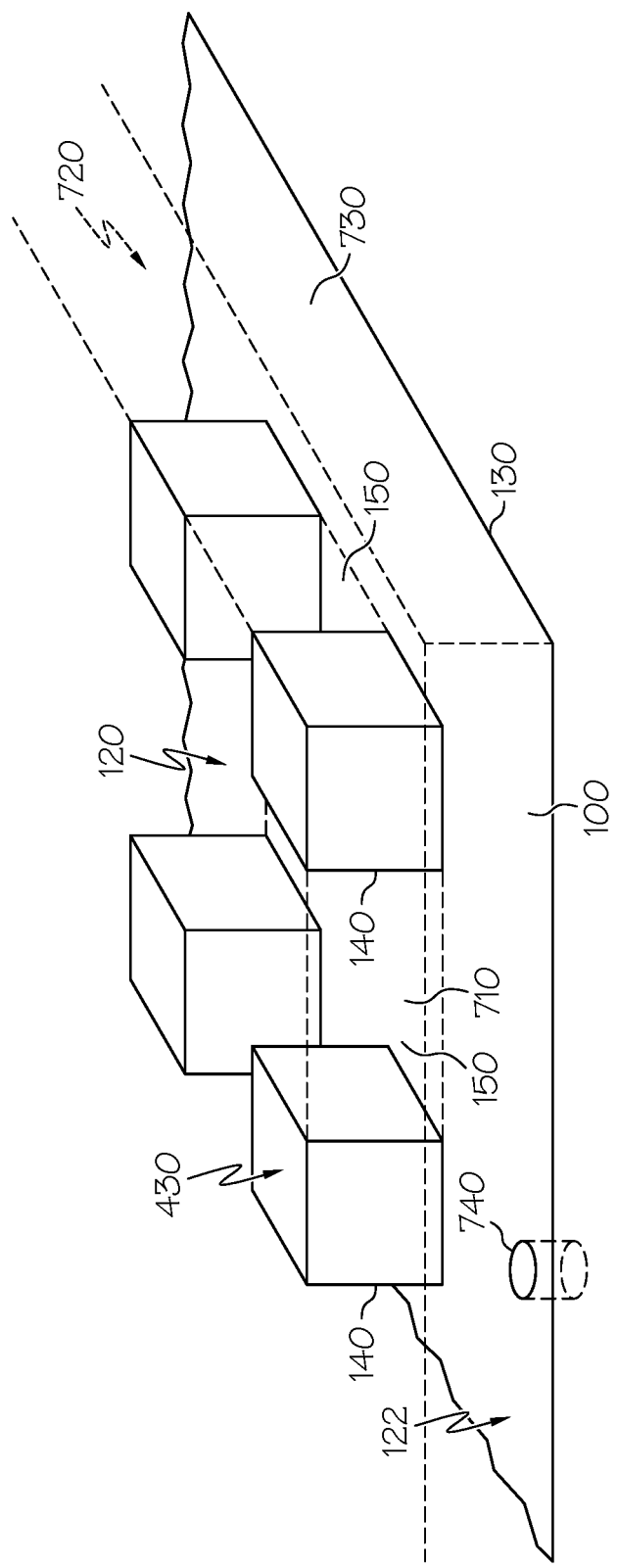
FIG. 8 is a schematic perspective view of part of a portion of a spinal interbody cage including pillars.
Figure 9:
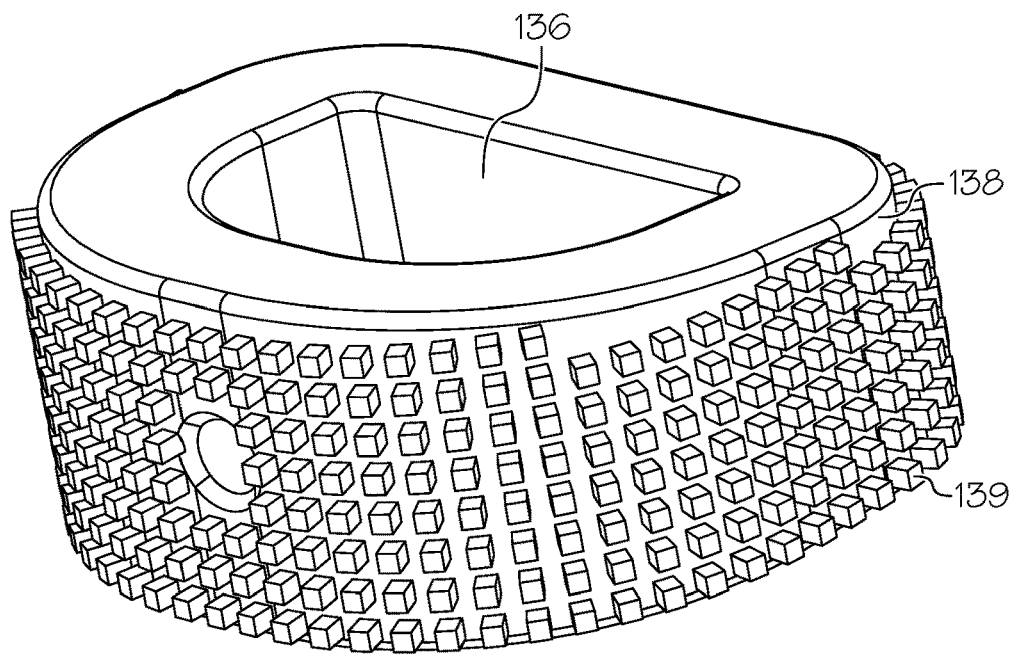
FIG. 9 is a top perspective view of a spinal interbody cage corresponding to an ALIF spinal interbody cage, in which the spinal interbody cage includes lateral exterior surface pillars (and in which pillars are not shown on the top face or the bottom face)
Figure 10:
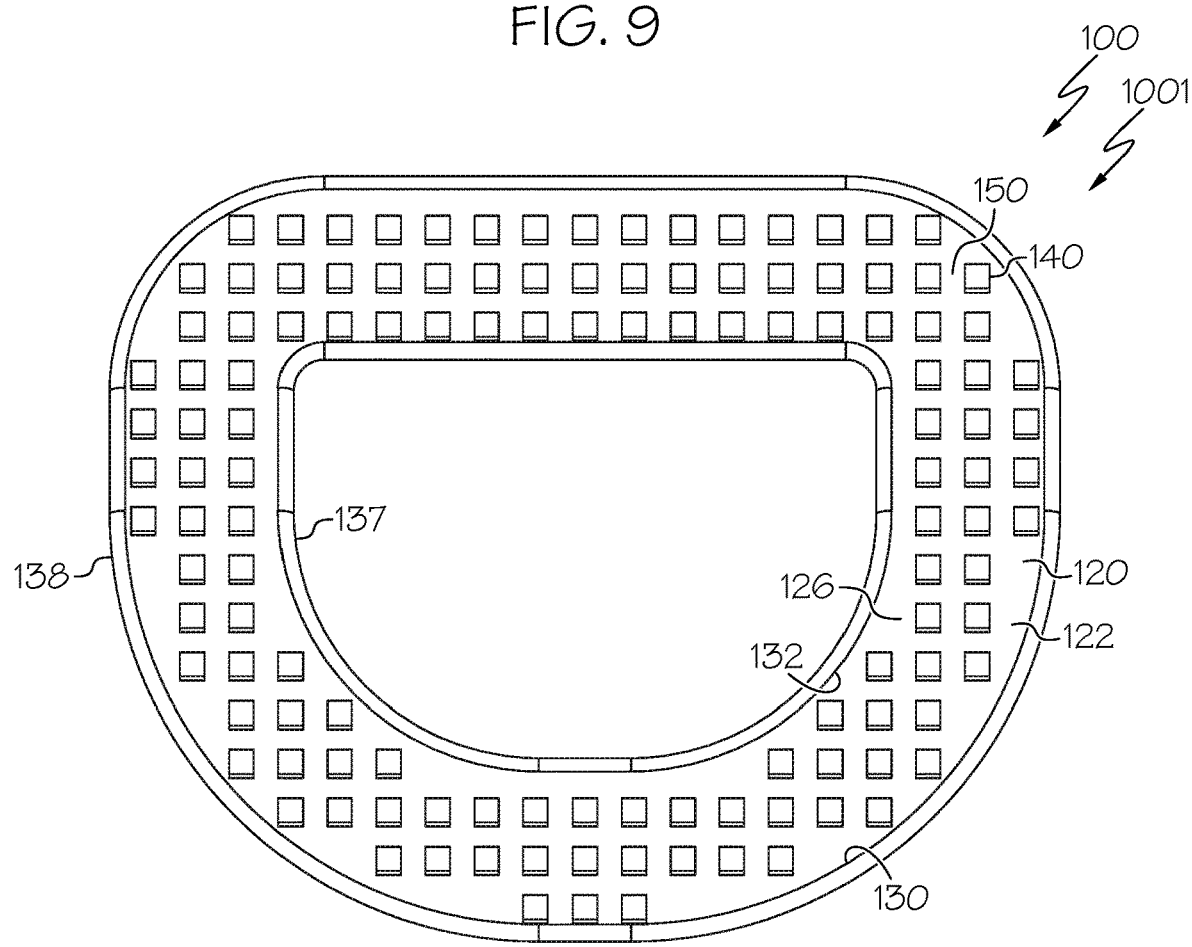
FIG. 10 is a top view of the ALIF spinal interbody cage of FIG. 1.
Figure 11:
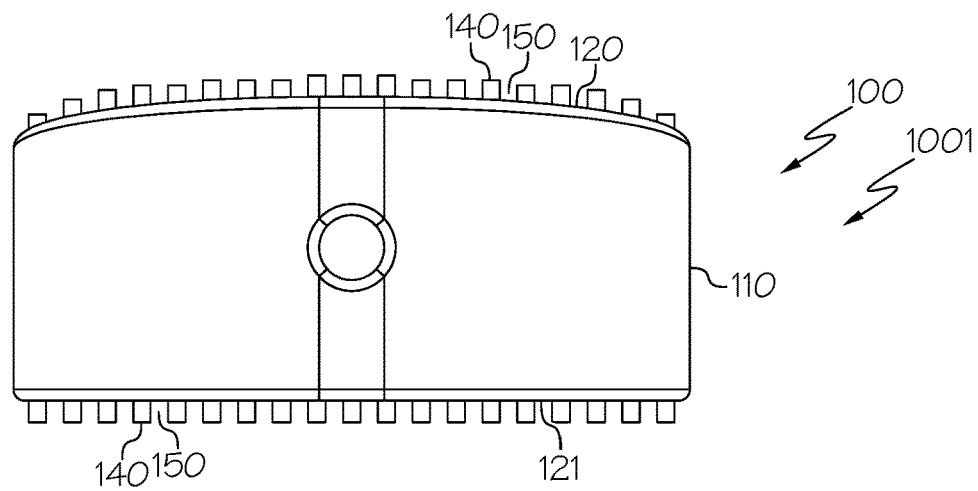
FIG. 11 is a first side view of the ALIF spinal interbody cage of FIG. 1.
Figure 12:
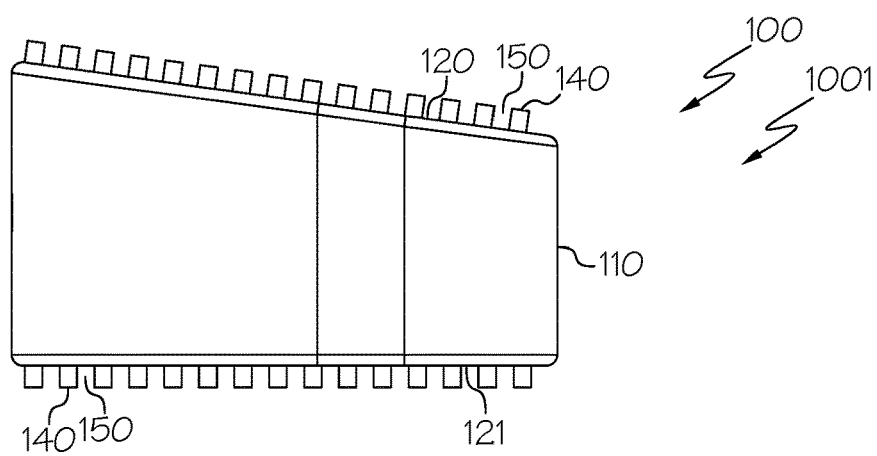
FIG. 12 is a second side view of the ALIF spinal interbody cage of FIG. 1.
Figure 13:
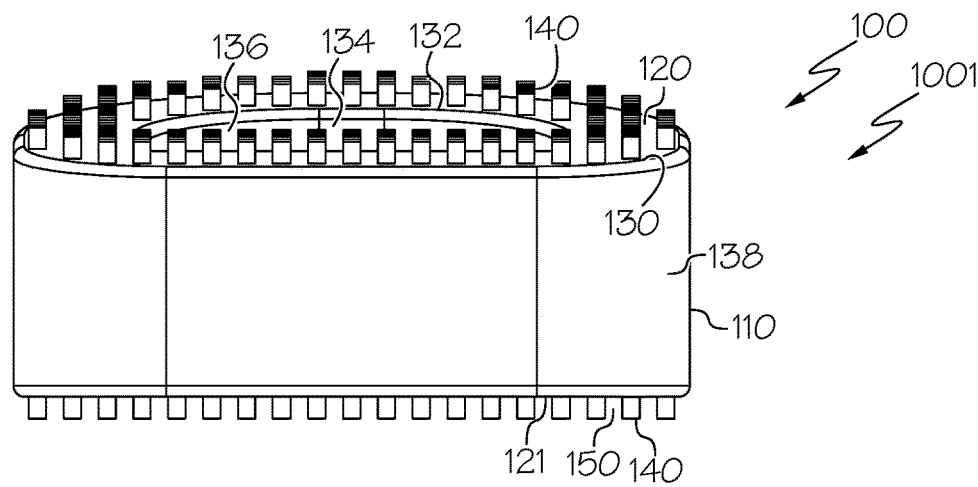
FIG. 13 is a third side view of the ALIF spinal interbody cage of FIG. 1.
Figure 14:
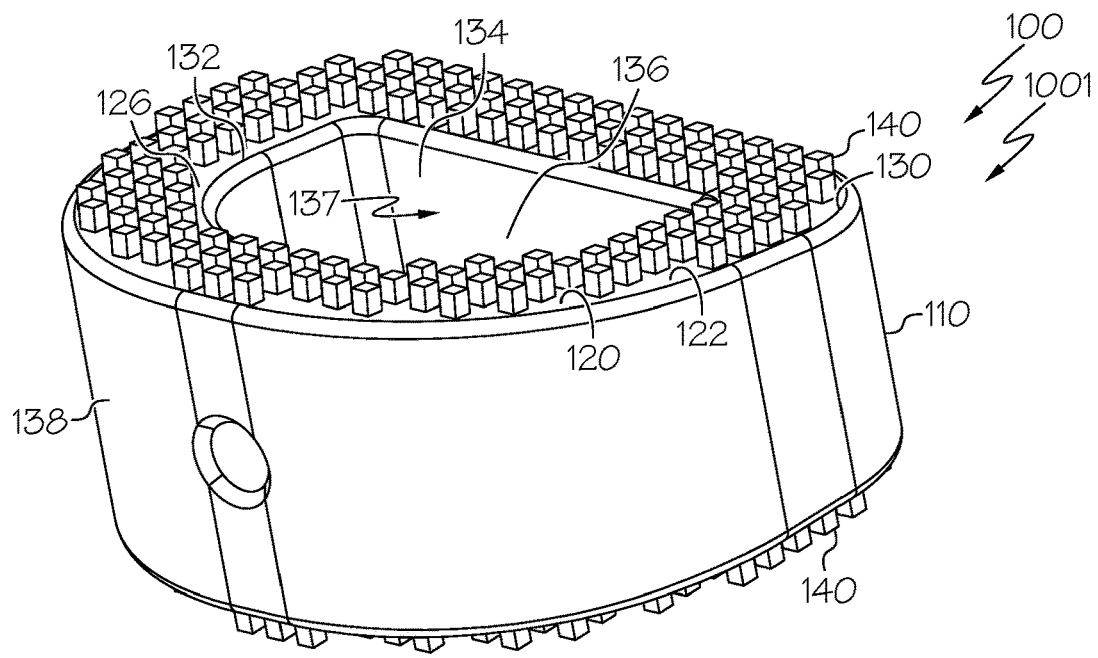
FIG. 14 is another top perspective view of the ALIF spinal interbody cage of FIG. 1.
Figure 15:
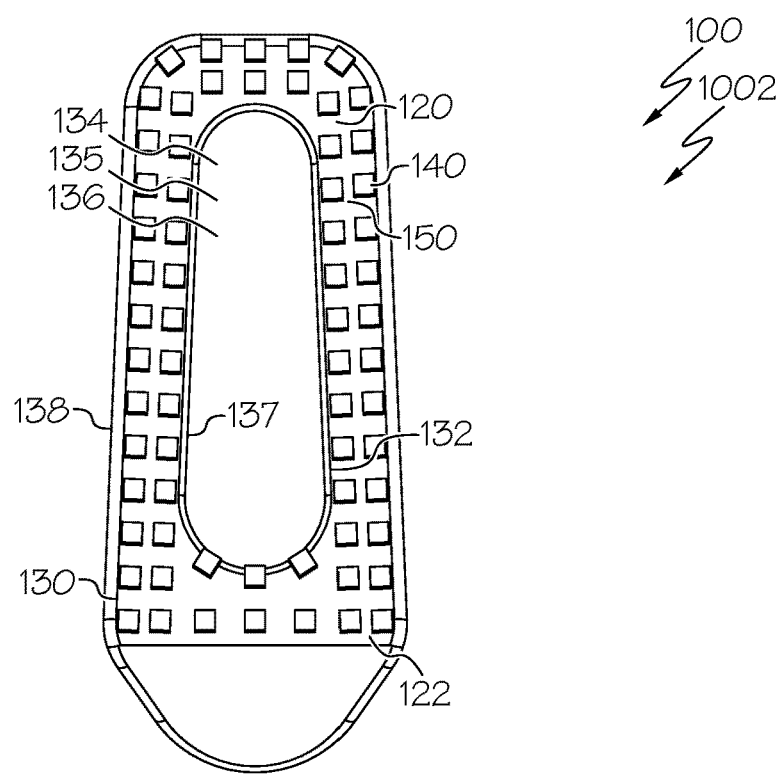
FIG. 15 is a top view of the PLIF spinal interbody cage of FIG. 2.
Figure 16:
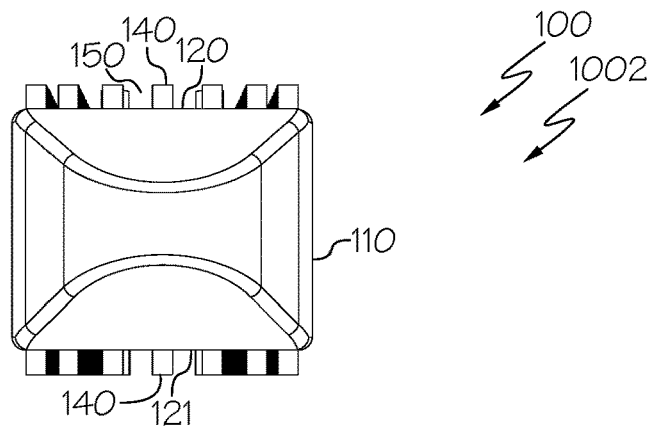
FIG. 16 is a first side view of the PLIF spinal interbody cage of FIG. 2.
Figure 17:
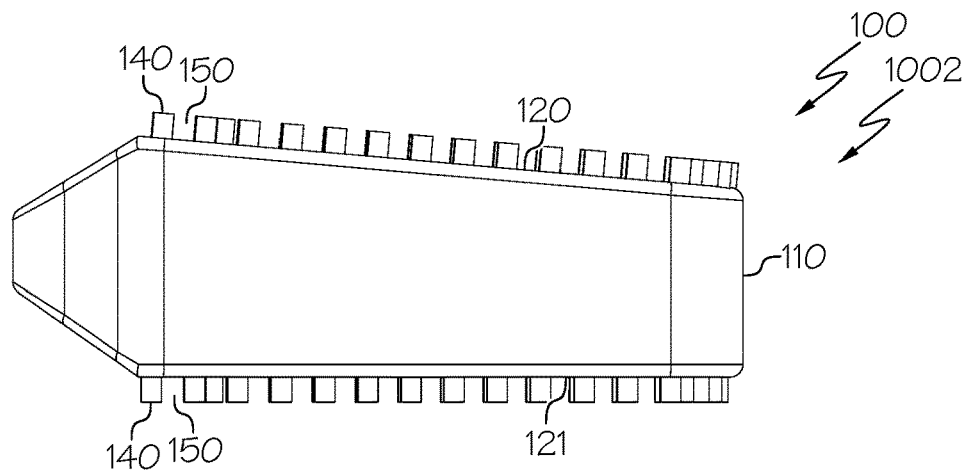
FIG. 17 is a second side view of the PLIF spinal interbody cage of FIG. 2.
Figure 18:
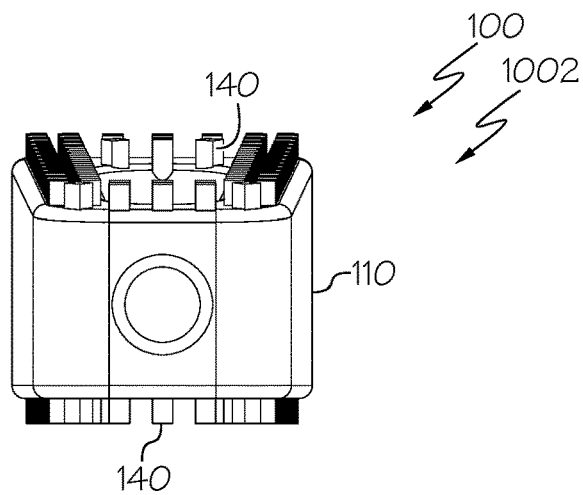
FIG. 18 is a third side view of the PLIF spinal interbody cage of FIG. 2.
Figure 19:
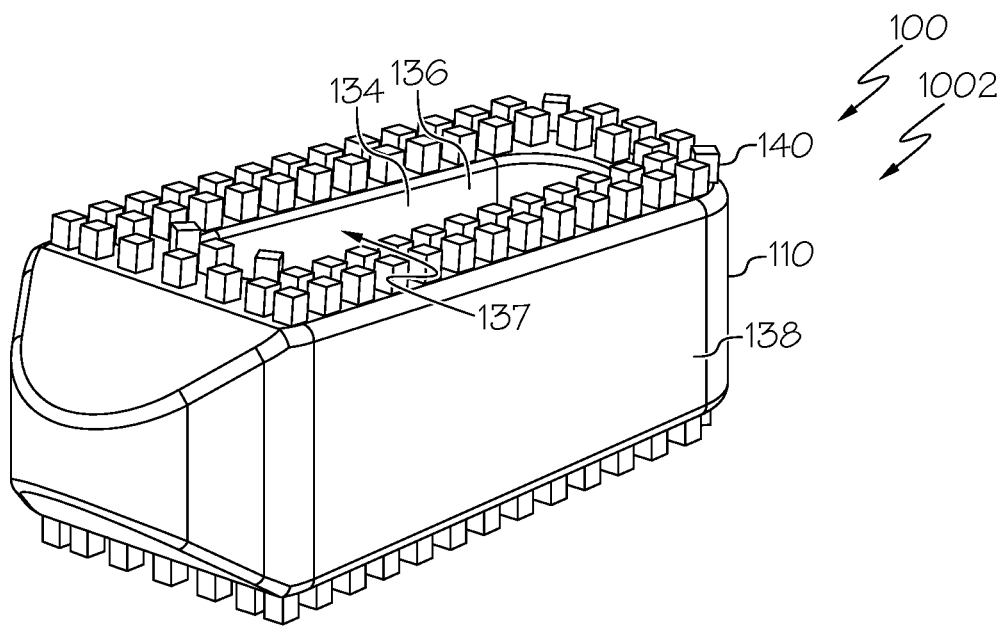
FIG. 19 is another top perspective view of the PLIF spinal interbody cage of FIG. 2.
Figure 20:
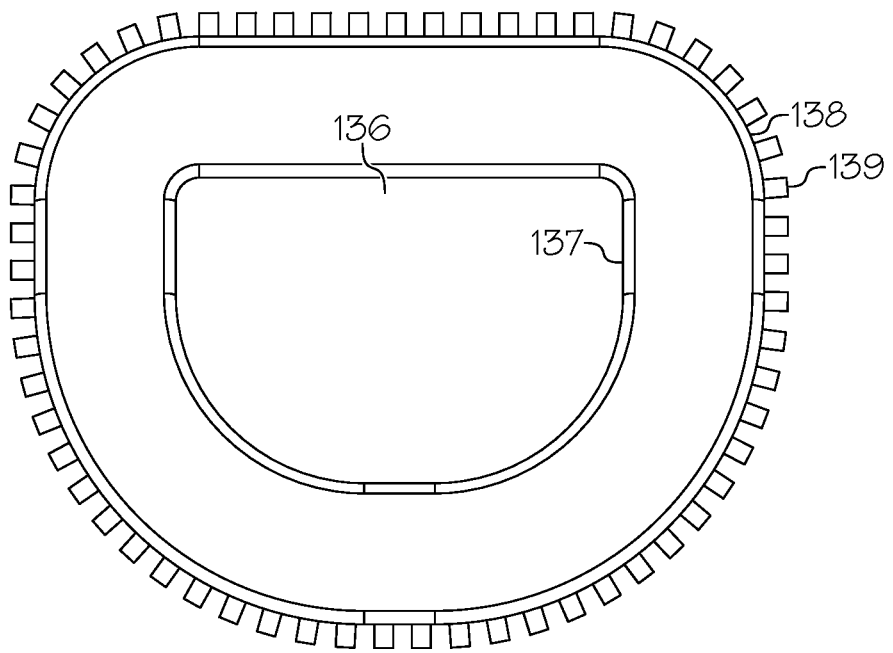
FIG. 20 is a top view of the ALIF spinal interbody cage of FIG. 9.
Figure 21:
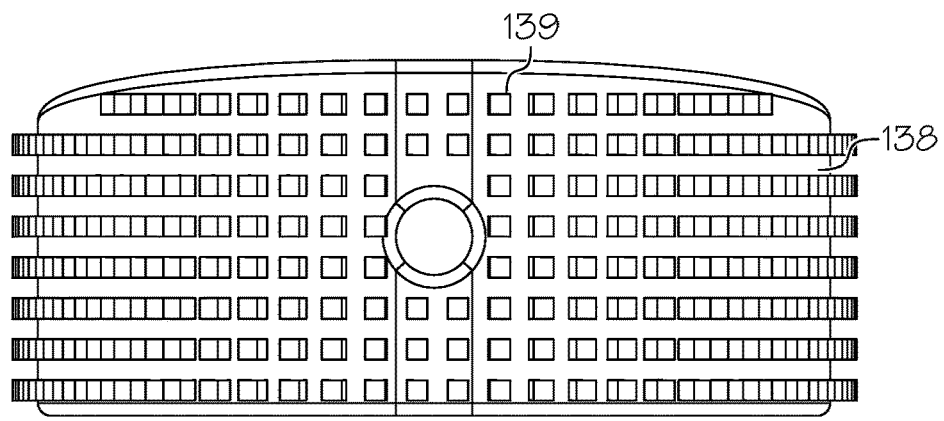
FIG. 21 is a first side view of the ALIF spinal interbody cage of FIG. 9.
Figure 22:
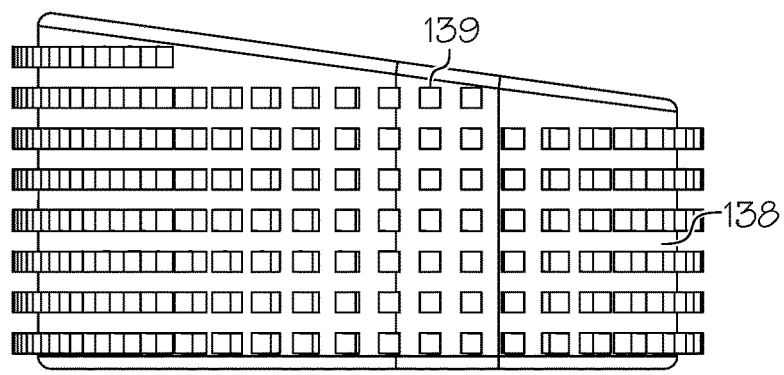
FIG. 22 is a second side view of the ALIF spinal interbody cage of FIG. 9.
Figure 23:
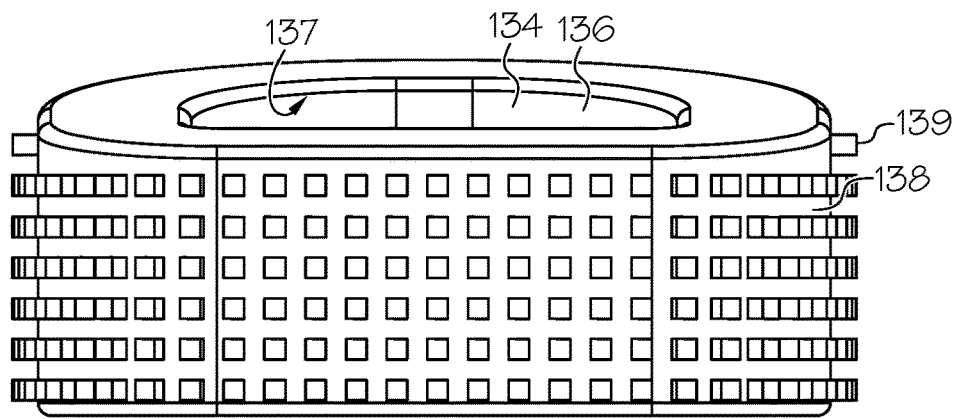
FIG. 23 is a third side view of the ALIF spinal interbody cage of FIG. 9.

More specifically, as shown in FIG. 8, considering the top face 120, the interface includes (i) the pillars 140, (ii) the slots 150 of the spinal interbody cage 100, which have a volume 710 and which, upon or following implantation, become occupied by bone of vertebral bodies and/or bone of bone graft, (iii) any additional space between the top face 120 and the spinal interbody cage 100 and a plane 720 defined by the distal ends 430 of the pillars 140, e.g. the space between the outer peripheral border 122 of the top face 120 that is not occupied by pillars 140 and the plane 720, as well as the space between the inner peripheral border 126 of the top face 120 that is not occupied by pillars 140 and the plane 720 (and thus not including space over the top central opening 134), which has a volume 730 and which also becomes occupied by bone of vertebral bodies and/or bone of bone graft, and (iv) any pores 740 on the top face 120, the bottom face 121, or the pillars 140, which, depending on their size, may also become occupied by bone of vertebral bodies and/or bone of bone graft. Turning to the bottom face 121, the interface also includes analogous features with respect to the bottom face 121.

Accordingly, for example, a ratio of the sum of (i) the volumes 710 of the slots 150 to (ii) the sum of the volumes 520 of the pillars 140 and the volumes 710 of the slots 150 of 0.40:1 would, following implantation of a spinal interbody cage 100 and subsequent remodeling and growth of bone of vertebral bodies and/or bone of bone graft, wherein the spinal interbody cage 100 includes an outer edge 130 and inner edge 132 of the top face 120, and an outer edge 131 and inner edge 133 of the bottom face 121, and for which pillars 140 are located at all of these edges, result in an interface that includes by volume 40% bone and 60% spinal interbody cage 100, and more particularly 60% pillars 140 of the spinal interbody cage 100. Similarly, a ratio of (i) the sum of the volumes 710 of the slots 150 to (ii) the sum of the volumes 520 of the pillars 140 and the volumes 710 of the slots 150 of 0.40:1 would, following implantation of a spinal interbody cage 100 and subsequent remodeling and growth of bone of vertebral bodies and/or bone of bone graft, wherein the spinal interbody cage 100 includes an outer edge 130 and inner edge 132 of the top face 120, and an outer edge 131 and inner edge 133 of the bottom face 121, and for which no pillars 140 are located at these edges, result in an interface that includes by volume more than 40% bone and less than 60% spinal interbody cage 100, with the percentage of bone increasing, and the percentage of spinal interbody cage 100 decreasing, with increasing distance between the peripheral-most pillars 140 and slots 150 and the edge 130 of the spinal interbody cage 100. By way of further examples, ratios of 0.51:1, 0.60:1, 0.70:1, 0.76:1, and 0.90:1, would result in interfaces that include, by volume, 51% bone and 49% spinal interbody cage 100, 60% bone and 40% spinal interbody cage 100, 70% bone and 30% spinal interbody cage 100, 76% bone and 24% spinal interbody cage 100, and 90% bone and 10% spinal interbody cage, respectively, for a spinal interbody cage 100 wherein the spinal interbody cage 100 includes such edges and for which pillars 140 are located at the edges. Moreover, the percentage of bone would increase, and the percentage of spinal interbody cage 100 would decrease, with increasing distance between the peripheral-most pillars 140 and slots 150 and the edge 130 of the spinal interbody cage 100. It is further believed that by achieving an interface that is at least 40% bone, but that has a sufficient amount of the spinal interbody cage 100 to provide support and to keep the spinal interbody cage 100 from migrating, that the interface will exhibit properties similar to those of the bulk bone of vertebral bodies adjacent to the interface, e.g. high resilience to compression, rotational shear, and vertical shear.

Considering example embodiments of the spinal interbody cage 100 in more detail, in one example embodiment, the Young's modulus of the spinal interbody cage 100 is 18 to 25 GPa and the ratio of (i) the sum of the volumes 710 of the slots 150 to (ii) the sum of the volumes 520 of the pillars 140 and the volumes 710 of the slots 150 is 0.51:1 to 0.60:1. In another example embodiment, the Young's modulus of the spinal interbody cage 100 is 100 to 110 GPa and the ratio of (i) the sum of the volumes 710 of the slots 150 to (ii) the sum of the volumes 520 of the pillars 140 and the volumes 710 of the slots 150 is 0.70:1 to 0.76:1. In another example embodiment, the spinal interbody cage 100 is made of implantable-grade polyetheretherketone with filler, the transverse area 510 of each pillar 140 is (350 µm×350 µm) to (450 µm×450 µm), the pillar height 420 of each pillar 140 is 400 to 600 µm, the slot width 152 of each slot 150 is 190 to 210 µm, and the ratio of (i) the sum of the volumes 710 of the slots 150 to (ii) the sum of the volumes 520 of the pillars 140 and the volumes 710 of the slots 150 is 0.85:1 to 1.6:1. In another example embodiment, the spinal interbody cage 100 is made of implantable-grade polyetheretherketone with filler, the transverse area 510 of each pillar 140 is (395 µm×395 µm) to (405 µm×405 µm), the pillar height 420 of each pillar 140 is 490 to 510 µm, the slot width 152 of each slot 150 is 190 to 210 µm, and the ratio of (i) the sum of the volumes 710 of (ii) the slots 150 to the sum of the volumes 520 of the pillars 140 and volumes 710 of the slots 150 is 0.92:1 to 1.4:1. In another example embodiment, the spinal interbody cage 100 is made of titanium, the transverse area 510 of each pillar 140 is (350 µm×350 µm) to (450 µm×450 µm), the pillar height 420 of each pillar 140 is 400 to 600 µm, the slot width 152 of each slot 150 is 390 to 410 µm, and the ratio of (i) the sum of the volumes 710 of the slots 150 to (ii) the sum of the volumes 520 of the pillars 140 and the volumes 710 of the slots 150 is 2.2:1 to 3.7:1. In another example embodiment, the spinal interbody cage 100 is made of titanium, the transverse area 510 of each pillar 140 is (395 µm×395 µm) to (405 µm×405 µm), the pillar height 420 of each pillar 140 is 490 to 510 µm, the slot width 152 of each slot 150 is 390 to 410 µm, and the ratio of (i) the sum of the volumes 710 of the slots 150 to (ii) the sum of the volumes 520 of the pillars 140 and the volumes 710 of the slots 150 is 2.4:1 to 3.5:1.

Considering additional example embodiments, in some embodiments the spinal interbody cage 100 has parallel profile. Also in some embodiments, the spinal interbody cage 100 has a lordotic profile. Also in some embodiments, the spinal interbody cage 100 has a domed profile.

In accordance with these embodiments, the pillars 140 may be understood to define a theoretical top surface of the spinal interbody cage 100, at the distal ends 430 of pillars 140 extending from the top face 120, and a theoretical bottom surface of the spinal interbody cage 100, at the distal ends 430 of pillars 140 extending from the bottom face 121 of the spinal interbody cage 100.

In this context, a spinal interbody cage 100 having a parallel profile has a theoretical top surface and a theoretical bottom surface that define top and bottom planes that are parallel with respect to each other and that have no height differences across the respective theoretical top and bottom surfaces. Of note, there may be localized variance from these parallel planes (e.g. a tapered leading edge to ease insertion of one or more tall pillars 140 that extend above the theoretical surface to provide enhanced initial fixation) but, in bulk (i.e. considering the majority of the pillars 140, and excluding pillars 140 that are outliers), the theoretical top and bottom surfaces define planes that are parallel with respect to each other.

Also in this context, a spinal interbody cage 100 having a lordotic profile has a theoretical top surface and a theoretical bottom surface that define planes that diverge with respect to each other and that have gradually increasing height differences across the respective surfaces when traversing from one end of the implant to the opposite end. Again, there may be localized variance from these diverging planes (e.g. a tapered leading edge to ease insertion of one or more tall pillars 140 that extend above the theoretical surface to provide enhanced initial fixation) but, in bulk, the theoretical top and bottom surfaces define planes that diverge with respect to each other.

Also in this context, a spinal interbody cage 100 having a domed profile has a theoretical top surface and/or a theoretical bottom surface that has an arched contour. The corresponding arch may be in a direction oriented with the length of the cage, in a direction oriented with the width of the cage, or in both directions. For example, the domed profile may be defined by a cylindrical shape in one direction or by an ovoid shape over the entire surface. The spinal interbody cage 100 may have a domed profile on top and a flat profile on bottom, or may have a domed profile on bottom and a flat profile on top, or may have domed profiles on both top and bottom. In some examples the domed surfaces may be defined on the spinal interbody cage 100 with essentially equal heights at distal and proximal ends of the spinal interbody cage 100 (a parallel profile with a domed top and/or bottom), or with distal and proximal heights being different (a lordotic profile with a domed top and/or bottom). Again, there may be localized variance from these domed profiles (e.g. a tapered leading edge to ease insertion of one or more tall pillars 140 that extend above the theoretical surface to provide enhanced initial fixation) but, in bulk, the theoretical top and/or bottom surfaces have an arched contour.

In some example embodiments, the pillars 140 are distributed and dimensioned to provide immediate micro-subsidence following implantation in a patient, between adjacent vertebral bodies, thereby providing post-operative interdigitated fixation and stability.

As shown in FIG. 9 and FIGS. 20-23, in some example embodiments, the spinal interbody cage 100 includes at least one lateral exterior surface 138 including lateral exterior surface pillars 139 extending therefrom. Also, in some example embodiments, the spinal interbody cage 100 includes at least one interior surface 137 including interior surface pillars extending therefrom (the interior surface pillars being like the lateral exterior surface pillars 139 but extending from the at least one interior surface 137 instead of from the at least one lateral exterior surface 138). Interior surface pillars may promote bridging of bone between adjacent vertebral bodies through the central cavity 136 of the spinal interbody cage 100. Also, in some of these examples, one or more of the interior surface pillars have heights that differ from those of other interior surface pillars. Interior surface pillars having different heights may promote better holding of bone graft within the central cavity 136 of the spinal interbody cage 100.

Indeed, also disclosed are spinal interbody cages like the spinal interbody cage 100 as disclosed above and as follows, but including pillars 140 extending from the top face 120 but not from the bottom face 121, or including pillars 140 extending from the bottom face 121 but not from the top face 120, or not including pillars 140 extending from the top face 120 or the bottom face 121. Further disclosed are such spinal interbody cages also including lateral exterior surface pillars 139 extending from at least one lateral exterior surface 138, or interior surface pillars extending from at least one interior surface 137, or both.

In some example embodiments, the pillars 140 include, at their distal ends 430, a roughened surface. The roughened surface may promote resistance of the pillars 140 to expulsion from bone of the adjacent vertebral bodies.

In some example embodiments, the transverse area 510 of one or more of the pillars 140 increases distally. For example, in some embodiments the transverse area 510 of at least 50%, at least 60%, at least 70%, at least 80%, at least 90%, at least 95%, or all of the pillars 140 increases distally. In accordance with these embodiments, the pillars 140 can be inversely tapered distally. This may promote gripping of the pillars 140 normal to the interface resulting from the implantation.

In some example embodiments, the transverse area 510 of one or more of the pillars 140 does not decrease distally. For example, in some embodiments the transverse area 510 of at least 50%, at least 60%, at least 70%, at least 80%, at least 90%, at least 95%, or all of the pillars 140 does not decrease distally. Also in some example embodiments, the transverse area 510 of one or more of the pillars 140 can be substantially constant along the vertical axis 410 along which the one or more pillars 140 extend distally. For example, in some embodiments the transverse area 510 of at least 50%, at least 60%, at least 70%, at least 80%, at least 90%, at least 95%, or all of the pillars 140 is substantially constant along the vertical axis 410 along which the one or more pillars 140 extend distally. In accordance with these embodiments, the distal end 430 of the one or more pillars 140 can have a distal end area, defined by the distal edges 432 of the one or more pillars 140, that is substantially equal to the transverse area 510 of the one or more pillars 140. This also may promote gripping of the pillars 140 normal to the interface resulting from the implantation.

As noted above, FIG. 1 and FIG. 2 provide illustrations in perspective view of various example spinal interbody cages 100, corresponding to an anterior lumbar interbody fusion (ALIF) spinal interbody cage 1001 and a posterior lumbar interbody fusion (PLIF) spinal interbody cage 1002. The ALIF spinal interbody cage 1001 and the PLIF spinal interbody cage 1002 exemplify spinal interbody cages 100 in which (1) the pillars 140 extend in a uniform direction, (2) a plurality of the pillars 140 are perpendicular to the top face 120 and a plurality of the pillars 140 are perpendicular to the bottom face 121, (3) the transverse area of each pillar is (250×250) $\mu m^2$ to (1,000×1,000) $\mu m^2$, (4) the height of each pillar is 300 to 1,000 μm, and (5) the width of each slot is 150 to 1,000 μm.

The spinal interbody cage 100 can be made from the materials noted above by methods such as laser cutting, injection molding, 3D printing, and other fabrication methods that are known in the art.

The spinal interbody cage 100 can be implanted between adjacent vertebral bodies, e.g. adjacent vertebral bodies from among C2-T1 vertebrae, adjacent vertebral bodies from among T1-T12 vertebrae, adjacent vertebral bodies of L4-L5 vertebra, and adjacent vertebral bodies of L5-S1 vertebrae, among others, by standard methods for implantation of spinal interbody cages.

In some embodiments, the implanting can be done such that bone graft is included within the spinal interbody cage 100, e.g. with the central cavity 136 of the spinal interbody cage 100. In accordance with these embodiments, the bone of bone graft can remodel and grow to fill in part or all space between the spinal interbody cage 100 and the adjacent vertebral bodies.

Also in some embodiments, additional hard tissue can be added to the top face 120, the bottom face 121, and/or the pillars 140 of the spinal interbody cage 100 prior to implanting. For example, shavings of hard-tissue of a patient, generated during preparation work including sawing or drilling of hard tissue of the patient, can be added. This may promote growth of tissue into slots 150 of the spinal interbody cage 100 following implantation.

Also in some embodiments, additional compositions can be added to the top face 120, the bottom face 121, and/or the pillars 140 of the spinal interbody cage 100 prior to implanting. Such compositions include, for example, blood, one or more antibiotics, one or more osteogenic compounds, bone marrow aspirate, and/or surface chemistry for inducing early bone ingrowth. For example, the top face 120, the bottom face 121, and/or the pillars 140 can be coated with one or more such compositions, with the pillars 140 retaining the compositions during implantation. This also may promote growth of tissue into slots 150 of the spinal interbody cage 100 following implantation.

Also, in some embodiments, the implanting can also be done without use of adhesives, e.g. cement or grout. Also, in some embodiments, the implanting can be done without use of screws.

Exemplary Embodiments

The following are exemplary embodiments of the spinal interbody cage, the method of making the spinal interbody cage, and the method of use of the spinal interbody cage as disclosed herein.

Embodiment A: A spinal interbody cage comprising:
(a) a bulk interbody cage;
(b) a top face being a top exterior surface of the bulk interbody cage and having a top central opening;
(c) a bottom face being a bottom exterior surface of the bulk interbody cage and having a bottom central opening;
(d) pillars for contacting vertebral bodies, the pillars being distributed on the top face, around the top central opening, and extending distally therefrom, and being distributed on the bottom face, around the bottom central opening, and extending distally therefrom, across areas of at least 25 mm$^2$ of each of the top face and the bottom face, respectively, each pillar being integral to the bulk interbody cage, having a distal end, having a transverse area of $(100\times100)$ to $(2,000\times2,000)$ µm$^2$, and having a height of 100 to 2,500 µm;
(e) slots to be occupied by bone of the vertebral bodies and/or by bone of a bone graft, the slots being defined by the pillars, the slots intersecting between the pillars, and each slot having a width of 100 to 2,500 µm as measured along the shortest distance between adjacent pillars; wherein:
the spinal interbody cage has a Young's modulus of elasticity of at least 3 GPa, and has a ratio of (i) the sum of the volumes of the slots to (ii) the sum of the volumes of the pillars and the volumes of the slots of 0.40:1 to 0.90:1.

Embodiment B: The spinal interbody cage of embodiment A, wherein the spinal interbody cage is made of one or more materials selected from implantable-grade polyaryletherketone that is essentially unfilled, implantable-grade polyetheretherketone, implantable-grade polyetherketoneketone, titanium, stainless steel, cobalt-chromium alloy, titanium alloy, Ti-6Al-4V titanium alloy, Ti-6Al-7Nb titanium alloy, ceramic material, silicon nitride (Si3N4), implantable-grade composite material, implantable-grade polyaryletherketone with filler, implantable-grade polyetheretherketone with filler, implantable-grade polyetheretherketone with carbon fiber, or implantable-grade polyetheretherketone with hydroxyapatite.

Embodiment C: The spinal interbody cage of embodiment A, wherein the spinal interbody cage is made of one or more other hard tissues selected from human hard tissue, animal hard tissue, autologous hard tissue, allogenic hard tissue, xenogeneic hard tissue, human cartilage, animal cartilage, human bone, animal bone, cadaver bone, or cortical allograft.

Embodiment D: The spinal interbody cage of embodiment A, wherein the spinal interbody cage is made of one or more materials selected from resin for rapid prototyping, SOMOS® NanoTool non-crystalline composite material, SOMOS® 9120 liquid photopolymer, SOMOS® WaterShed XC 11122 resin, ACCURA® XTREME™ White 200 plastic, or ACCURA® 60 plastic.

Embodiment E: The spinal interbody cage of any of embodiments A-D, wherein the spinal interbody cage has a parallel profile.

Embodiment F: The spinal interbody cage of any of embodiments A-D, wherein the spinal interbody cage has a lordotic profile.

Embodiment G: The spinal interbody cage of any of embodiments A-D, wherein the spinal interbody cage has a domed profile.

Embodiment H: The spinal interbody cage of any of embodiments A-G, wherein the pillars extend in a uniform direction.

Embodiment I: The spinal interbody cage of any of embodiments A-G, wherein one or more pillars extend at an angle and/or in a direction that differs from that of other pillars.

Embodiment J: The spinal interbody cage of any of embodiments A-I, wherein a plurality of the pillars are perpendicular to the top face and a plurality of the pillars are perpendicular to the bottom face.

Embodiment K: The spinal interbody cage of any of embodiments A-J, wherein the transverse area of each pillar is $(250\times250)$ µm$^2$ to $(1,000\times1,000)$ µm$^2$.

Embodiment L: The spinal interbody cage of any of embodiments A-K, wherein the height of each pillar is 300 to 1,000 µm.

Embodiment M: The spinal interbody cage of any of embodiments A-L, wherein the width of each slot is 150 to 1,000 µm.

Embodiment N: The spinal interbody cage of any of embodiments A-M, wherein the Young's modulus of the spinal interbody cage is 18 to 25 GPa and the ratio of (i) the sum of the volumes of the slots to (ii) the sum of the volumes of the pillars and the volumes of the slots is 0.51:1 to 0.60:1.

Embodiment O: The spinal interbody cage of any of embodiments A-M, wherein the Young's modulus of the spinal interbody cage is 100 to 110 GPa and the ratio of (i) the sum of the volumes of the slots to (ii) the sum of the volumes of the pillars and the volumes of the slots is 0.72:1 to 0.76:1.

Embodiment P: The spinal interbody cage of any of embodiments A-M, wherein the spinal interbody cage is made of implantable-grade polyetheretherketone with filler, the transverse area of each pillar is $(350\times350)$ to $(450\times450)$ µm$^2$, the height of each pillar is 400 to 600 µm, the width of each slot is 190 to 210 µm, and the ratio of the sum of (i) the volumes of the slots to (ii) the sum of the volumes of the pillars and the volumes of the slots is 0.51:1 to 0.60:1.

Embodiment Q: The spinal interbody cage of any of embodiments A-M, wherein the spinal interbody cage is made of titanium, the transverse area of each pillar is $(350\times350)$ to $(450\times450)$ µm$^2$, the height of each pillar is 400 to 600 µm, the width of each slot is 390 to 410 µm, and the ratio of (i) the sum of the volumes of the slots to (ii) the sum of the volumes of the pillars and the volumes of the slots is 0.72:1 to 0.76:1.

Embodiment R: The spinal interbody cage of any of embodiments A-Q, wherein the bulk interbody cage is non-porous.

Embodiment S: The spinal interbody cage of any of embodiments A-R, wherein the pillars are non-porous.

Embodiment T: The spinal interbody cage of any of embodiments A-S, wherein one or more pillars have dimensions that differ from those of other pillars, such that the transverse areas and/or heights, and thus volumes, of the one or more pillars differ from those of the other pillars.

Embodiment U: The spinal interbody cage of embodiment T, wherein the spinal interbody cage provides an endplate profile based the heights of the one or more pillars differing from those of the other pillars, and the spinal interbody cage having a parallel height.

Embodiment V: The spinal interbody cage of any of embodiments A-U, wherein the pillars are distributed and dimensioned to provide immediate micro-subsidence following implantation in a patient, between adjacent vertebral bodies, thereby providing post-operative interdigitated fixation and stability.

Embodiment W: The spinal interbody cage of any of embodiments A-V, wherein the spinal interbody cage comprises at least one lateral exterior surface comprising lateral exterior surface pillars extending therefrom.

Embodiment X: The spinal interbody cage of any of embodiments A-W, wherein the spinal interbody cage comprises at least one interior surface comprising interior surface pillars extending therefrom.

Embodiment Y: The spinal interbody cage of embodiment X, wherein one or more of the interior surface pillars have heights that differ from those of other interior surface pillars.

Embodiment Z: The spinal interbody cage of any of embodiments A-Y, wherein the pillars comprise, at their distal ends, a roughened surface.

Embodiment AA: The spinal interbody cage of any of embodiments A-Z, wherein the transverse area of one or more of the pillars increases distally.

Embodiment BB: The spinal interbody cage of any of embodiments A-Z, wherein the transverse area of one or more of the pillars does not decrease distally.

Embodiment CC: The spinal interbody cage of any of embodiments A-Z, wherein the transverse area of one or more of the pillars is substantially constant along the vertical axis along which the one or more pillars extend distally.

Embodiment DD: The spinal interbody cage of any of embodiments A-BB, wherein the spinal interbody cage is selected from the group consisting of an anterior lumbar interbody fusion (ALIF) spinal interbody cage, a posterior lumbar interbody fusion (PLIF) spinal interbody cage, a lateral spinal interbody cage, a direct lateral interbody fusion (DLIF) spinal interbody cage, a transforaminal lumbar interbody fusion (TLIF) spinal interbody cage, an extreme lateral interbody fusion (XLIF) spinal interbody cage, and a cervical spinal interbody cage.

It will be apparent to those skilled in the art that various modifications and variations can be made without departing from the spirit and scope of the claimed invention.

What is claimed is:

1. A spinal interbody cage comprising:
(a) a bulk interbody cage;
(b) a top face being a top exterior surface of the bulk interbody cage and having a top central opening;
(c) a bottom face being a bottom exterior surface of the bulk interbody cage and having a bottom central opening;
(d) pillars for contacting vertebral bodies, the pillars being distributed on the top face, around the top central opening, and extending distally therefrom, and being distributed on the bottom face, around the bottom central opening, and extending distally therefrom, across areas of at least 25 mm² of each of the top face and the bottom face, respectively, each pillar being integral to the bulk interbody cage, having a distal end, having a transverse area of (100×100) to (2,000×2,000) μm², and having a height of 100 to 2,500 μm; and
(e) slots to be occupied by bone of the vertebral bodies and/or by bone of a bone graft, the slots being defined by the pillars, the slots intersecting between the pillars such that each of the slots intersects at least one of the other slots, and each slot having a width of 100 to 2,500 μm as measured along the shortest distance between adjacent pillars; wherein:
the spinal interbody cage has a Young's modulus of elasticity of at least 3 GPa, and has a ratio of (i) the sum of the volumes of the slots to (ii) the sum of the volumes of the pillars and the volumes of the slots of 0.40:1 to 0.90:1; and
each pillar has at least two adjacent lateral sides that face adjacent pillars.

2. The spinal interbody cage of claim 1, wherein the spinal interbody cage is made of one or more materials selected from implantable-grade polyaryletherketone that is essentially unfilled, implantable-grade polyetheretherketone, implantable-grade polyetherketoneketone, titanium, stainless steel, cobalt-chromium alloy, titanium alloy, Ti-6Al-4V titanium alloy, Ti-6Al-7Nb titanium alloy, ceramic material, silicon nitride (Si3N4), implantable-grade composite material, implantable-grade polyaryletherketone with filler, implantable-grade polyetheretherketone with filler, implantable-grade polyetheretherketone with carbon fiber, or implantable-grade polyetheretherketone with hydroxyapatite.

3. The spinal interbody cage of claim 1, wherein the spinal interbody cage is made of one or more other hard tissues selected from human hard tissue, animal hard tissue, autologous hard tissue, allogenic hard tissue, xenogeneic hard tissue, human cartilage, animal cartilage, human bone, animal bone, cadaver bone, or cortical allograft.

4. The spinal interbody cage of claim 1, wherein the spinal interbody cage has a parallel profile.

5. The spinal interbody cage of claim 1, wherein the spinal interbody cage has a lordotic profile.

6. The spinal interbody cage of claim 1, wherein the spinal interbody cage has a domed profile.

7. The spinal interbody cage of claim 1, wherein the transverse area of each pillar is (250×250)μm² to (1,000×1,000)μm².

8. The spinal interbody cage of claim 1, wherein the height of each pillar is 300 to 1,000 μm.

9. The spinal interbody cage of claim 1, wherein the width of each slot is 150 to 1,000 μm.

10. The spinal interbody cage of claim 1, wherein the bulk interbody cage is non-porous.

11. The spinal interbody cage of claim 1, wherein the pillars are non-porous.

12. The spinal interbody cage of claim 1, wherein:
one or more pillars have dimensions that differ from those of other pillars, such that the transverse areas and/or heights, and thus volumes, of the one or more pillars differ from those of the other pillars; and
the spinal interbody cage provides an endplate profile based on the heights of the one or more pillars differing from those of the other pillars, and the spinal interbody cage having a parallel height.

13. The spinal interbody cage of claim 1, wherein the pillars are distributed and dimensioned to provide immediate micro-subsidence following implantation in a patient, between adjacent vertebral bodies, thereby providing post-operative interdigitated fixation and stability.

14. The spinal interbody cage of claim 1, wherein the spinal interbody cage comprises at least one lateral exterior surface comprising lateral exterior surface pillars extending therefrom.

15. The spinal interbody cage of claim 1, wherein the spinal interbody cage comprises at least one interior surface comprising interior surface pillars extending therefrom.

16. The spinal interbody cage of claim 15, wherein one or more of the interior surface pillars have heights that differ from those of other interior surface pillars.

17. The spinal interbody cage of claim 1, wherein the pillars comprise, at their distal ends, a roughened surface.

18. The spinal interbody cage of claim 1, wherein the transverse area of one or more of the pillars increases distally.

19. The spinal interbody cage of claim 1, wherein the transverse area of one or more of the pillars is substantially constant along the vertical axis along which the one or more pillars extend distally.

20. The spinal interbody cage of claim 1, wherein the spinal interbody cage is selected from the group consisting of an anterior lumbar interbody fusion (ALIF) spinal interbody cage, a posterior lumbar interbody fusion (PLIF) spinal interbody cage, a lateral spinal interbody cage, a direct lateral interbody fusion (DLIF) spinal interbody cage, a transforaminal lumbar interbody fusion (TLIF) spinal interbody cage, an extreme lateral interbody fusion (XLIF) spinal interbody cage, and a cervical spinal interbody cage.

\* \* \* \* \*

UNITED STATES PATENT AND TRADEMARK OFFICE
CERTIFICATE OF CORRECTION

PATENT NO. : 11,324,606 B2
APPLICATION NO. : 16/492328
DATED : May 10, 2022
INVENTOR(S) : George J. Picha et al.

It is certified that error appears in the above-identified patent and that said Letters Patent is hereby corrected as shown below:

On the Title Page

Item (73) Assignee:
"Gary A. Zwick" should read -- GARY A. ZWICK, TRUSTEE OF THE EVEREST TRUST UTA APRIL 20, 2017 --

In the Specification

Column 11, Line 24, "(100 µm × 100 µm) to (2,000 µm × 2,000 µm)" should read -- (i) (100 µm × 100 µm) to (2,000 µm × 2,000 µm) --

Signed and Sealed this
Twenty-fifth Day of April, 2023

Katherine Kelly Vidal
*Director of the United States Patent and Trademark Office*